(12) United States Patent
Braun et al.

(10) Patent No.: US 11,674,895 B2
(45) Date of Patent: Jun. 13, 2023

(54) SYSTEM AND METHOD FOR MONITORING AN AIR-SPACE OF AN EXTENDED AREA

(71) Applicant: GRANDPERSPECTIVE GmbH, Berlin (DE)

(72) Inventors: René Braun, Berlin (DE); Peter Maas, Leipzig (DE)

(73) Assignee: GRANDPERSPECTIVE GmbH, Kleinmachnow (DE)

( * ) Notice: Subject to any disclaimer, the term of this patent is extended or adjusted under 35 U.S.C. 154(b) by 0 days.

(21) Appl. No.: 17/641,255

(22) PCT Filed: Sep. 8, 2020

(86) PCT No.: PCT/EP2020/075073
§ 371 (c)(1),
(2) Date: Mar. 8, 2022

(87) PCT Pub. No.: WO2021/048122
PCT Pub. Date: Mar. 18, 2021

(65) Prior Publication Data
US 2022/0334056 A1 Oct. 20, 2022

(30) Foreign Application Priority Data
Sep. 9, 2019 (DE) .................. 10 2019 124 092.1

(51) Int. Cl.
*G01N 21/3504* (2014.01)
*G01N 33/00* (2006.01)
*G06Q 50/26* (2012.01)
*G01N 21/35* (2014.01)

(52) U.S. Cl.
CPC ..... *G01N 21/3504* (2013.01); *G01N 33/0027* (2013.01); *G01N 2021/3595* (2013.01); *G06Q 50/265* (2013.01)

(58) Field of Classification Search
CPC .......... G01N 21/3504; G01N 33/0027; G01N 2021/3595
See application file for complete search history.

(56) References Cited

U.S. PATENT DOCUMENTS 4,795,253 A * 1/1989 Sandridge ............. G01J 3/0208
250/338.5
7,411,196 B2 8/2008 Kalayeh
(Continued)

FOREIGN PATENT DOCUMENTS

CN 106338484 A 1/2017
DE 3887768 T2 5/1994
(Continued)

OTHER PUBLICATIONS

Bonow et al., "Gas leak localization in industrial environments using a TDLAS based remote gas sensor and autonomous mobile robot with the Tri-Max method", IEEE, 2013, pp. 987-992, vol. 978-1-4673-5643, International Conference on Robotics and Automation (ICRA), Karlsruhe, Germany.
Harig et al., "Scanning infrared remote sensing system for identification, visualization, and quantification of airborne pollutants", SPIE, Feb. 2002, pp. 1-12, vol. 4754, Society of Photo-Optical Instrumentation Engineers.
Braun, "A Sixth Sense", World Fertilizer, Sep. 2020, pp. 1-5.
Rutkauskas et al., "Autonomous multi-species environmental gas sensing using drone-based Fourier-transform Infrared spectroscopy", Optics Express, Apr. 2019, pp. 9578-9587, vol. 27, No. 7.

*Primary Examiner* — David P Porta
*Assistant Examiner* — Meenakshi S Sahu
(74) *Attorney, Agent, or Firm* — The Webb Law Firm

(57) ABSTRACT

The invention relates to a system for monitoring an airspace for an extensive area, with at least two optical sensors with a passive Fourier transform infrared spectrometer, wherein
(Continued)

each optical sensor has an adjustable monitoring range and wherein the monitoring ranges of the at least two optical sensors overlap at least in sections, having a server for evaluating the measurement data and for controlling the at least two optical sensors, the server being set up to monitor the optical sensors for automatic scanning of the monitored areas, wherein the server assigns a respective solid angle to the measurement data on the basis of the position data of the optical sensor, evaluates the measurement data of the optical sensors to derive the spectral intensity distribution of the received IR radiation for each solid angle and, by means of correlation of the intensity distribution with known gas spectra, to identify at least one target substance, in the event of an incident, if a first optical sensor identifies a target substance in a first solid angle, to control at least one further optical sensor, to scan the overlap region with the monitoring region of the first optical sensor, to identify the target substance from the measurement data of the at least one further optical sensor and, in the event of an incident, to control at least one further optical sensor, to scan the overlap region with the monitoring region of the first optical sensor, to identify the target substance from the measurement data of the at least one further optical sensor, identifying at least one further solid angle with an infrared signal of the target substance, and determining the coordinates of the overlap region with increased concentration of the target substance from the solid angle information of the first solid angle and of the at least one further solid angle, wherein the measurement signals of the at least one further optical sensor in spatial directions with too small a measurement radius are not included in the evaluation.

12 Claims, 14 Drawing Sheets

(56) References Cited

U.S. PATENT DOCUMENTS

| | | |
|---|---|---|
| 2017/0097274 A1 | 4/2017 | Thorpe et al. |
| 2018/0292286 A1 | 10/2018 | Dittberner et al. |
| 2019/0034868 A1 | 1/2019 | Konanur et al. |
| 2019/0137388 A1 | 5/2019 | Mallery et al. |
| 2020/0116583 A1 | 4/2020 | Hedberg |

FOREIGN PATENT DOCUMENTS

| | | |
|---|---|---|
| EP | 2088409 B1 | 6/2014 |
| JP | 564078134 A | 3/1989 |
| JP | 2009505099 A | 2/2009 |
| JP | 2011204118 A | 10/2011 |
| JP | 2019504993 A | 2/2019 |

* cited by examiner

SYSTEM AND METHOD FOR MONITORING AN AIR-SPACE OF AN EXTENDED AREA

CROSS-REFERENCE TO RELATED APPLICATIONS

This application is the United States national phase of International Application No. PCT/EP2020/075073 filed Sep. 8, 2020, and claims priority to German Patent Application No. 10 2019 124 092.1 filed Sep. 9, 2019, the disclosures of which are hereby incorporated by reference in their entirety.

BACKGROUND OF THE INVENTION

Field of the Invention

The invention relates to a system and method for monitoring an airspace

Description of Related Art

For an area such as industrial chemical plants, ports or critical transport infrastructure. The invention also relates to an optical sensor, in particular for use in the system and for the method. In particular, the invention is for the detection and localisation of gas leaks and potentially hazardous gas clouds.

On the above-mentioned areas, leaks or malfunctions of equipment can cause gases to escape that are harmful to the environment, can lead to accidents with far-reaching consequences, and can pose risks to the health and lives of people staying on the area.

Common monitoring of an area is done with chemo-electric sensors that are sensitive to only one gas or a small number of chemical gases at a time. In addition, the sensors must be located where the gases are present in the ambient air. Therefore, the number of sensors to be used is high.

Furthermore, the use of Fourier transform infrared spectrometers (FTIR) is known, which can determine the composition of the observed solid angle above the area for the presence of various chemical gases in short time intervals. This can be used to detect the unwanted escape of gases and to determine the location by means of triangulation. However, the known methods lack a good spatial resolution and thus a reliable localisation of the leakage point, especially when visibility is impaired by topographical obstacles.

An FTIR spectrometer known from the prior art serves as the optical sensor. The spectrometer itself is stationary and its infrared optics are aligned at an upward angle. The ambient light is directed onto the infrared optics by means of a swivelling mirror and thus the environment is scanned. However, the monitoring range is limited to a small solid angle range.

EP 2 088 409 B1 discloses an imaging spectrometer for remote sensing to produce a spectrally resolved image, but without a spatial resolution of the measured area.

U.S. Pat. No. 4,795,253 A discloses the continuous monitoring of gaseous materials present in the vicinity of production facilities, in which three detectors determine the immediate environment above an emission source by triangulation.

SUMMARY OF THE INVENTION

Therefore, the present invention is based on the technical problem of improving a system and method for monitoring an airspace for an extended area.

According to the invention, the aforementioned technical problem is solved by a system, by a method and by an optical sensor of the type and manner described below.

According to a first teaching of the invention, the system for monitoring an airspace of an area is equipped with at least two optical sensors with a passive Fourier transform infrared spectrometer and with a server for evaluating the measurement data and for controlling the at least two optical sensors, wherein each optical sensor has an adjustable monitoring range and wherein the monitoring ranges of the at least two optical sensors overlapping at least in sections, and wherein the server is set up, to control the optical sensors in the normal case for an automatic scanning of the monitored areas, wherein the server assigns to the measurement data in each case a solid angle on the basis of the position data of the optical sensor, deriving the spectral intensity distribution of the received IR radiation from the measurement data of the optical sensors for each solid angle and identifying at least one target substance by means of correlation of the intensity distribution with known gas spectra, in case of an incident, when a first optical sensor identifies a target substance in a first solid angle, to control at least one further optical sensor to scan the overlapping area with the monitoring area of the first optical sensor, identifying from the measurement data of the at least one further optical sensor at least one further solid angle with an infrared signal of the target substance, and determining the coordinates of the overlap area with increased concentration of the target substance from the solid angle information of the first solid angle and the at least one further solid angle. The system is characterised in that the monitoring range of each optical sensor has different measuring radii due to the topography and/or the development of the area as a result of shadowing depending on the solid angle, and the monitoring range of each optical sensor is defined by the solid angle range and the associated measuring radii and that the measurement signals of the at least one further optical sensor in spatial directions with too small a measurement radius are not included in the evaluation.

The system is understood in such a way that it is sufficient, in particular but not only for larger systems with a plurality of optical sensors, if the monitoring areas of at least two optical sensors each overlap at least in sections. Thus, an overlapping of the monitoring areas is necessarily required in pairs, but not of all pairs of optical sensors. An overall system can thus also be understood as a combination of several systems in which the monitoring areas of all of the at least two optical sensors overlap at least in sections.

The aforementioned server can also be referred to as an evaluation unit or as an evaluation and control unit.

The server can preferably also have several sub-units that are separate from each other, which are preferably each integrated in an optical sensor or at least arranged adjacent to it. For example, each sensor can have one subunit, which together form the server or the evaluation unit. Furthermore, various tasks of the server can be performed by subunits. For example, a first subunit of the server can evaluate the measurement data and a second subunit can control one or more optical sensors.

In a preferred embodiment, the server is designed as a central control unit that controls two or more optical sensors and/or evaluates the measurement data from two or more optical sensors. Particularly preferably, the central control unit controls all sensors and/or evaluates the measurement data of all optical sensors of the system. Preferably, the server may be located at a large spatial distance from the optical sensors. Furthermore, the server can also be a changing server of a server network. For example, the evaluation of the measurement data and/or the control of the optical sensors can also be performed using a cloud provided by one or more servers.

Within a solid angle, the measuring radius corresponds to the maximum distance up to which the optical sensor can record a measuring signal. The measuring radius can be the maximum measuring radius that the optical sensor can realise. However, the measuring radius can also be limited in its spatial extension, i.e. shorter, due to shadowing by an obstacle. The optical sensor can therefore not generate measurement data for the area behind the obstacle in this solid angle. The measurement radii per solid angle are determined and set during the installation of the system for the optical sensors based on the known topography and/or development of the area.

The measuring radii of the optical sensors are preferably adjustable depending on the solid angle. The measuring radius is set for each solid angle starting from the optical sensor up to the maximum distance or up to an obstacle causing shadowing. Preferably, the system is designed to automatically define the measurement radii for the solid angles, preferably from two- and/or three-dimensional map data. For example, and preferably, the system may be set up to define the measurement radii using a digital twin and/or a simplified three-dimensional model of the area to be monitored. Further preferably, the system is set up to acquire obstacle information by means of a camera of the optical sensor and to define the measurement radii using the obstacle information. The obstacle information preferably corresponds to optical obstacles, which are preferably arranged along an optical axis of the sensor. Particularly preferably, the system is set up to define the measurement radii using obstacle information from multiple optical sensors.

A solid angle is further understood to be a spatial solid angle range that the optical sensor can resolve. The solid angle range of a solid angle, i.e. the spatial resolution of the optical sensor, can be adjustable within the system. For each solid angle of the solid angle range, the associated measurement radius thus corresponds to the maximum distance up to which the optical sensor can record a measurement signal. For all solid angles of the solid angle range, the optical sensor can receive optical signals and provide corresponding measurement signals.

Thus, measurement signals from an optical sensor are only used if the associated measurement radius of the optical sensor extends to a required overlapping range with the monitoring range of another optical sensor.

The server is preferably set up for one of the functions described above even if only one component of the server is set up for one of the functions described above. For example, the server can be set up as an evaluation unit to control the optical sensors to automatically scan the monitoring areas and/or to assign a solid angle to the measurement data based on the position data of the optical sensor. Thus, if a first optical sensor identifies a target substance, the server controls a further sensor to scan an overlapping area of the monitoring area of the first sensor with the monitoring area of the further sensor. Preferably, this allows the system to verify an identification of the target substance by the first optical sensor.

Furthermore, the server is set up to replace the measurement signals of the at least one further optical sensor which have not been included in the evaluation by a weighted mathematical interpolation of spatially adjacent measurement signals. Adjacent measurement signals are measurement signals that are provided for solid angles that are spatially adjacent in the solid angle range to the solid angle with too small a measurement radius.

Furthermore, at least three optical sensors are provided and the server is set up to select, in the event of an incident, at least one further optical sensor for activation whose monitoring range has a maximum overlap with the monitoring range of the first optical sensor.

Preferably, the server is set up to match a solid angle of the first optical sensor for which the target substance is identified with the monitoring ranges of the further sensors and to select a further optical sensor for actuation whose monitoring range overlaps the monitoring range of the first sensor for that solid angle for which the first optical sensor identifies the target substance.

In a preferred manner, the server is set up not to use a selected optical sensor if the position of the selected optical sensor is in the direction of the solid angle range of the first optical sensor with detected target substance. In such a case, the next best optical sensor is preferably selected that has the largest possible overlap with the monitoring range of the first optical sensor.

In this way, it can be achieved that the optical axis of the first sensor for the solid angle for which the target substance is identified and the optical axis of the further optical sensor, which is controlled to scan the overlapping area, are arranged at an angle to each other. From the solid angles of the optical sensors for which the target substance is identified, a position of the target substance can then be determined, preferably by means of triangulation.

Furthermore, it is advantageous if the server is set up to determine the column densities of the target substance from the measurement data of the optical sensors, wherein the column density is the mathematical product of the concentration of the gas (measured in ppm) and the spatial length of the gas cloud (measured in m) and wherein the server is set up to determine the coordinates of the overlapping area of the highest column densities of different optical sensors.

In a preferred embodiment, the system and in particular the server is set up to determine a column density of the target substance in the first solid angle and to determine a column density of the target substance in solid angles adjacent to the first solid angle by means of the first optical sensor in the event of an incident. Solid angles adjacent to the first solid angle preferably continuously adjoin the first solid angle. However, it is also preferred that an adjacent solid angle has a predefined angular distance from the first solid angle. For example, if the first solid angle has a value of 45°, adjacent solid angles may have values of 44° and 46°.

According to a preferred further development, the system, and in particular the server, is set up to identify from the first solid angle and the adjacent solid angles the solid angle with the highest column density of the target substance and to determine, by means of the first optical sensor, a column density of the target substance in a solid angle adjacent to the solid angle with the highest column density. The system is thus set up to compare the column densities of the target substance determined in the first step and assigned to the solid angles and to determine that solid angle at which the highest column density of the target substance is determined. Subsequently, the column density of the target substance is determined again for a solid angle adjacent to this solid angle of the highest target substance column density. Preferably, a solid angle with unknown column density of the target substance is selected as the adjacent solid angle. For example, if the highest column density of the target substance is determined at a solid angle of 44° as described above, the column density of the target substance is then determined for a solid angle with a value of 43°.

Preferably, the system and in particular the server is set up to determine the solid angle of the monitoring area of the first optical sensor that has the highest column density of the target substance in the event of an incident. For this purpose, the system is set up to carry out the steps described above until that solid angle is determined for which the column density of the target substance is maximum. If, for example, a lower column density of the target substance is determined at 43° and 45° than for a solid angle of 44°, the solid angle with the value of 44° is the solid angle of the monitoring area that has the highest column density of the target substance. However, the system can also be designed to determine several local maxima of the column density of the target substance in the monitoring area.

Preferably, the system and in particular the server is set up to determine a first concentration gradient of the target substance corresponding to the solid angles of the first optical sensor in the event of an incident. The concentration gradient is a measure of the change in target substance column density per discrete solid angle step.

In a preferred further development, the system and in particular the server is set up to determine a multi-dimensional concentration gradient of the target substance in the event of an incident from the first concentration gradient corresponding to the solid angles of the first optical sensor and an analogous further concentration gradient of a further optical sensor. Preferably, concentration gradients are determined for the solid angles of a plurality of sensors and combined by the system to determine the multi-dimensional concentration gradient. For example, the multi-dimensional concentration gradient can be a measure of the change in target substance column density in a first spatial direction and in a spatial direction perpendicular to the first spatial direction.

Preferably, the system and in particular the server is set up to compare the determined column density of the target substance with a target substance limit value. Particularly preferably, the system and especially the server is set up to trigger an alarm if the determined column density of the target substance exceeds the target substance limit value, preferably for a predefined period of time.

The acquisition of measurement data representing the column densities of the respective solid angles can also take place before determining the respective column densities from this measurement data. For example, an optical sensor can acquire measurement data for several solid angles and the determination of the column densities present at the respective solid angles or the solid angle that has the highest column density of the target substance is then carried out by the server in its function as an evaluation unit. Preferably, the acquisition of measurement data and the determination of the column densities and/or the highest column density can also take place simultaneously or partially simultaneously.

In a preferred manner, the server is further set up to control the optical sensors for measurements with increased spatial scanning in the event of an incident. In doing so, the scanning speed is slowed down and, if necessary, the measurement duration for a solid angle is increased in order to obtain a better signal-to-noise ratio.

Preferably, the server is further set up to determine the coordinates of the overlap area of the highest column densities of various optical sensors and to link the coordinates with a map representation and to create a two-dimensional representation of the incident and/or to link the coordinates with the images of a video camera and to create a visual representation of the incident. This creates quick and clear information for the operator of the system.

Furthermore, at least one active infrared radiation source can be provided and an optical sensor picks up the infrared light along a defined measuring path. This increases the measuring accuracy of the system along these measuring paths.

The term "the server is set up" means that the server is designed as a computer with a computer environment, whereby suitable microchips, memory chips or storage media as well as interfaces to external, if necessary also remote devices are provided and whereby at least one computer program is present in order to technically realise the described functions.

In a further preferred manner, at least one stationary detector can be provided in the previously described system, whereby the server is set up to use an output signal of the at least one stationary detector as a triggering signal for the deployment of the optical sensors in the spatial area of the stationary sensor. Thus, in the event of an incident, the identification of the target substance can be triggered using the stationary measurement data. If the stationary detector is located in the area of a leakage within the system, the measurement signal of the stationary detector can be used to determine the incident in a specific room area and thus activate or trigger the use of the optical sensors described above.

Furthermore, the system can have a plurality of stationary detectors in the monitoring area to monitor a plurality of possible leakage points and thus trigger the use of the optical sensors in different spatial areas.

In a further preferred manner, the system can be set up to select a stationary detector corresponding to the first solid angle of the first optical sensor from the plurality of detectors in the event of an incident. The system checks the plausibility of the identification of the target substance if the stationary detector also identifies a target substance. Alternatively or additionally, it may be provided that the system is set up to receive stationary measurement data from an external stationary detector in order to plausibilise an identification of the target substance. In this way, the system can advantageously be retrofitted to an existing gas monitoring system with one or more stationary detectors. Stationary measurement data from the external stationary detectors can thus also be used by the system according to the invention. The control of the stationary detector can preferably be a reception of measurement data of the stationary detector, a retrieval of measurement data of the stationary detector, an activation of the stationary detector for the acquisition of measurement data and/or a reception and/or retrieval of measurement data from an evaluation unit connected to the stationary detector.

Preferably, the stationary detector is designed as electrochemical detectors, also referred to as gas sensors, PID detectors (photoionisation detectors), FID detectors (flame ionisation detectors), heat tone detectors, Dräger chip measuring systems (CMS), also referred to as for optoelectronic detection of reaction products of gases, direct-reading Dräger tubes, multi-gas measuring instruments with several individual detectors, also of different designs, infrared sensors designed as small gas measuring cells with broadband IR radiation and a double detector (measuring and reference detector), laser spectroscope detectors, infrared cameras with filters, UV and VIS spectrometers (e.g. grating spectrometers or spectrometers with optical slit), LIDAR sensors, photoacoustic spectroscopy detectors, Near-infrared detectors, acoustic detectors for leak detection, mass spectrometers, ion mobility spectrometers or as gas chromatographs.

The previously explained embodiments have optical sensors and detectors that are installed in a fixed location within the plant to be monitored or on the premises to be monitored and are thus arranged in a fixed spatial relationship to one another.

In a further preferred embodiment of the system, at least one sensor can be designed as a mobile sensor, wherein the mobile sensor is designed as an optical sensor or as a detector.

The mobile sensor can be hand-carried, on an earth-bound remote-controlled or manned vehicle, or moved by means of an aerial vehicle such as a drone. Preferably, the mobile sensor is adapted to take measurements during the movement. Furthermore, the system is preferably set up to assign measurement data and/or measurement signals detected by the mobile sensor to a corresponding position value of the mobile sensor.

If the mobile sensor is itself an optical sensor of the type described above, then the optical sensor can form the system as a second sensor together with a first stationary optical sensor.

If the mobile sensor is designed as a detector described above, then the concentration of the target substance or substances can be measured directly by the at least one detector in a spatial area of the incident detected by the at least two optical sensors. This on-site measurement can serve a plausibility check of the data determined by the system or also a concrete determination of concentrations on site.

Preferably, the system is thus set up, in the incident that the first optical sensor identifies a target substance in a first solid angle, to move the mobile sensor into the monitoring range of the first sensor in order to identify a target substance.

The above-mentioned technical problem is solved according to a further teaching of the invention by a system for monitoring an airspace of an area with at least one optical sensor with a passive Fourier transform infrared spectrometer and with a server for evaluating the measurement data and for controlling the at least one optical sensor, wherein the at least one optical sensor has an adjustable monitoring range, wherein at least one mobile airworthy detector is provided and wherein the server is set up, to control the optical sensor to automatically scan the monitoring areas, wherein the server assigns a spatial angle to the measurement data in each case on the basis of the position data of the optical sensor, to derive the spectral intensity distribution of the received IR radiation for each solid angle from the measurement data of the optical sensor and identifying at least one target substance by means of correlation of the intensity distribution with known gas spectra, and, in case of an incident, when the optical sensor identifies a target substance in a solid angle, to detect the concentration of the target substance along the solid angle identified by the optical sensor with the at least one mobile detector in a location-dependent manner.

Thus, the system, and preferably the server, is set up to move the mobile detector to locate the target substance in the monitoring area of the first sensor. Preferably, the system is set up to move the mobile detector along a predetermined path through the monitoring area. Preferably, the predetermined path may be a grid. Preferably, the system is set up to move the mobile detector along a trajectory corresponding to an optical axis of the first optical sensor in the first solid angle. The system preferably locates the target substance by determining that position of the mobile detector in the monitoring area of the first sensor for which the concentration of the target substance is maximum.

The above-mentioned system uses optical sensors for monitoring an airspace of an area preferably with an FTIR spectrometer for the detection of target substances, with infrared optics for imaging a partial section of the airspace of the area to be monitored onto the FTIR spectrometer, with a video camera and with a positioning unit for aligning the sensor unit formed by the FTIR spectrometer, the infrared optics and the camera, wherein the infrared optics and the camera detect an equal solid angle, in particular wherein the optical axes of the infrared optics and the camera are aligned parallel to each other.

This specifies an optical sensor that can be adjusted as a whole to different solid angles and thus has almost no restrictions on the directions of observation. Thus, the optical sensor is smaller and can be installed more easily than is the case with optical sensors with FTIR spectrometers known from the prior art.

In particular, the infrared optics is designed as a Cassegrain telescope with a parabolic mirror and a secondary mirror. The design as a Cassegrain telescope simplifies the imaging of the partial section of the airspace to be monitored and, due to the use of the parabolic mirror, leads to an increased intensity of the recorded radiation and thus also of the FTIR signal.

In an advantageous way, the camera is arranged laterally to the infrared optics. Therefore, the camera, which is also to image the partial section of the area, can have a telephoto lens if necessary and produce a magnified image. The camera then does not interfere with the optical path of the infrared optics, but has a parallax that must be compensated for an accurate superimposition of the measurement results with the camera image.

Alternatively, the camera can also be arranged in the optical axis of the infrared optics, in particular at or in front of the secondary mirror. In this way, the camera can record the video image without parallax displacement and without influencing the optical path of the infrared optics.

Another alternative is that the camera is designed as a camera system with a camera arranged laterally to the infrared optics and with a camera arranged in the optical axis of the infrared optics. This combines the advantages of the two cameras, the lateral camera can generate a high-resolution image and the camera arranged in the optical axis serves for parallax-free image generation.

Preferably, the positioning unit comprises a communication device and is set up to align the sensor unit on the basis of control commands received by the communication device.

The positioning unit is thus a remotely controllable positioning unit, preferably designed for wireless reception of control signals. In a preferred embodiment, the remotely controllable positioning unit has an antenna unit for receiving control signals and for transmitting measurement data and/or measurement signals. In this way, a physical connection of the optical sensors can be avoided. Installation of the system is then possible quickly and easily even with a large distance between the optical sensors. Optical sensors with a remotely controllable positioning unit can also have a physical or wired power supply.

Preferably, the optical sensor has a communication device for receiving and/or transmitting signals. Signals can be analogue and/or digital signals. The communication device can be wired and/or wireless.

Preferably, the communication device is designed to receive and/or transmit signals via WLAN or mobile radio, in particular GPRS, UMTS, LTE, LTE-Advanced, 5G. Preferably, the positioning unit is set up to automatically move the infrared optics for scanning an overlapping area with a monitoring area of another sensor using the received signals.

Preferably, the optical sensor is adapted to receive target detection signals from a further sensor and, in response to a target detection signal, automatically scan an overlap area with a monitoring area of the further sensor to detect a target. The target substance detection signal comprises at least information that the further sensor has identified a target substance. Further, the target substance detection signal preferably comprises the solid angle for which the further sensor has identified the target substance. Preferably, the optical sensor is arranged to transmit a target detection signal in response to identifying a target substance in its monitoring area. A receiving of a target detection signal may be an indirect receiving via a unit, for example a server, as an alternative or supplement to a direct receiving from a further optical sensor.

In accordance with a further teaching of the invention, the technical problem outlined above is also solved by a method for monitoring an airspace of an area, in which at least two optical sensors with a passive Fourier transform infrared spectrometer are used to monitor the area at least in sections, in which each optical sensor detects adjustable solid angle ranges within a monitoring area, in which the monitoring area of an optical sensor overlaps at least in sections with the monitoring area of at least one further optical sensor, in which the optical sensors are usually triggered to automatically scan the monitored areas, in which the spectral intensity distribution of the received IR radiation is derived from the measurement data of the optical sensors for each solid angle and a correlation of the intensity distribution with known gas spectra is carried out, in which, in the event of an incident, when an infrared signal of a target substance is identified by a first optical sensor in a first solid angle, at least one further optical sensor is triggered to scan the overlapping area with the monitoring area of the first optical sensor, in which at least one further solid angle with an infrared signal of the target substance is identified from the measurement data of the at least one further optical sensor, and in which the coordinates of the overlap area with increased concentration of the target substance are determined from the solid angle information of the first solid angle and of the at least one further solid angle. The method is characterised in that the monitoring range of each optical sensor has different measuring radii due to the topography and/or the area of the terrain as a result of shadowing depending on the solid angle and the monitoring range of each optical sensor is determined and fixed by the solid angle range and the associated measuring radii and that measurement signals of the at least one further optical sensor in spatial directions with too small a measurement radius are not included in the evaluation.

When carrying out the method, at least one optical sensor described above can be used in particular.

In a preferred manner, the measurement signals of the at least one further optical sensor that have not been included in the evaluation are replaced by mathematical interpolation of adjacent measurement signals.

Furthermore, at least three optical sensors can be used, wherein an infrared signal of a target substance is identified by the first sensor in the first solid angle and wherein, in the event of an incident, at least the further optical sensor is selected for activation whose monitoring range has a maximum overlap with the monitoring range of the first optical sensor.

In this context, it is advantageous if a selected optical sensor is not used if the position of the selected optical sensor lies in the direction of the solid angle range of the first optical sensor with detected target substance. This is because in this case there is no sufficient angle for triangulation between the solid angle of the detected target substance and the necessary solid angle of the further optical sensor. In such a case, the next best optical sensor can then be selected that has the greatest possible overlap with the monitoring range of the first optical sensor.

Furthermore, it is preferred that the column density is calculated as the mathematical product of the concentration of the gas (measured in ppm) and the length of the gas cloud (measured in m). Thus, a detected target substance can be assigned a concentration after the length of the cloud has been determined with the previously described method.

In a further preferred manner, in the event of an incident, the optical sensors are triggered for measurements with increased spatial scanning and/or the coordinates of the overlap area of the highest column densities of various optical sensors are determined and/or the coordinates are linked to a map representation and a two-dimensional representation of the incident is created and/or the coordinates are linked to the images of a video camera and a visual representation of the incident is created and/or the infrared light from an optical sensor is recorded with at least one active infrared radiation source.

A method is preferred in which stationary measurement data, preferably stationary measurement data from an external stationary sensor, are received and in which, in the event of an incident, the identification of the target substance is checked for plausibility using the stationary measurement data.

Thus, for the systems and methods described above, it has been recognised that by driving an additional optical sensor, an accuracy of detection of target materials can be significantly increased. Furthermore, it has been recognised that in an area with a topography that impairs the free view of the optical sensors, the localisation of the disturbance incident can be carried out quickly and reliably if the topography of the area is taken into account when installing the system for determining the monitoring areas. This is because not only the spatial directions, but also the associated measurement radii, which are limited by the area, by buildings and/or by other technical installations, are used to determine the monitoring areas. This is because the optical sensors can only measure as far as there is a clear view. The localisation of the disturbance incident is then only carried out with the measurement data whose spatial extents actually overlap.

In the following, the described system, the optical sensor and the described procedure are explained in detail.

The described systems and methods are used for near-real-time identification and localisation of gas leaks and for map-based situation assessment for emergency services in the event of an incident, as well as for continuous emission and immission measurement of gaseous hazardous substances within or along the perimeter of a monitoring area.

The systems, which can also be called airspace monitoring systems, are based on the networking of at least two, but in principle any number of passive, freely positionable FTIR remote sensing spectrometers as optical sensors to form a bi- or multi-perspective overall system.

Optionally, passive infrared spectroscopy can be combined with individual active infrared measuring sections.

The passive measurement technique enables the area-wide scanning of a large monitoring area or the airspace. The addition of individual active measurement sections enables the highly accurate background concentration determination of a large number of gases (emission and immission measurement) as well as an extended target substance library and lower detection limits along the predefined active measurement sections. Active and passive modes can be operated independently of each other and with the same optical sensor.

The structure of the system is explained below.

At selected locations, preferably with a good overview of the area to be monitored, e.g. on roofs, chimneys or masts, optical sensors are installed in the open air, fixed but freely positionable in terms of their orientation, for continuous monitoring. In passive applications, an optical sensor enables a measuring radius of up to approx. 1-4 km, depending on the desired local resolution and assuming a clear view. The scanning speeds and the achievable resolutions are mutually dependent; a typical scanning speed of a 360° scan is in the range of 1 to 10 minutes. Therefore, paths are defined in the application that are traversed by an optical sensor during scanning. Critical parts of the system are scanned more intensively, i.e. with larger solid angle ranges than is required for administrative buildings, for example, which may even be completely or partially removed from the path.

To enable the procedural combined evaluation of the at least two optical sensors, the monitoring areas of at least some of the optical sensors overlap. Optionally, the active infrared radiation sources are permanently installed along selected measuring sections at distances of up to several hundred metres and aligned with the optical sensor assigned to them.

In routine cases, the optical sensors work decentralized and autonomously, but the measurement data preferably converge in a server as a central system, which enables combined evaluation and control as an overall system.

The optical sensors represent individual measuring points of the remote gas detection system and use FTIR spectrometers for the remote detection of gases in combination with infrared optics for reducing the field of view of the spectrometer, a positioning unit for aligning the spectrometer as well as a video camera and evaluation and control software preferably stored in the optical sensor or in the external server in one of the previously explained embodiments. The positioning unit allows free alignment in 360° azimuth and at least +/−60° elevation.

The FTIR spectrometer is preferably not triggered by the positioning unit, but provides a continuous stream of measurement data. However, it can also be provided that the optical sensor only continuously provides measurement data in the event of an incident and provides measurement data for regularly spaced solid angles during a scan. For example, measurement data could be provided in 2° steps, whereby evaluation capacities can be saved compared to continuous measurement data acquisition. The positioning unit thus moves the FTIR spectrometer together with the infrared optics and the camera as one sensor unit. By adjusting the angular velocity of the positioning unit, the spatial sampling of the measurement is controlled. By assigning the position time stamp of the positioning unit, the measurement data is assigned to a solid angle. In addition, a measurement time stamp can be assigned to record a temporal development of the target substance cloud.

A video camera, which is aligned with the FTIR spectrometer as part of the optical sensor, provides a video image in the direction of view of the FTIR spectrometer either continuously or at predefined positions. Neighbouring video images can be stitched together using a stitching algorithm to form a coherent video image of any size and display format up to a 360° panoramic view.

By superimposing chemical or spectroscopic information, i.e. the measurement results with the video image, a two-dimensional spatially resolved gas distribution is visualised from the measurement data. A bilinear interpolation of the measurement results in X- and Y-direction, i.e. over the two-dimensional image scanned by the optical sensor, and the additional or alternative superimposition with a video image, provides an intuitively graspable two-dimensional view of the identified gas cloud.

Independent of the settings of the measured angular ranges, the display of the result images for freely selectable partial ranges within the measured angular range is possible in freely selectable display ratios.

Over time, the optical sensor generates a stream of result images and a stream of time and spatial angle stamped measurement results.

Remote gas sensing using infrared spectroscopy measures long-wave infrared radiation and evaluates the measured infrared spectrum for the presence of known spectral signatures of target substances. In this way, gaseous target substances can be identified and also quantified from great distances of up to several kilometres.

The FTIR spectrometer receives infrared radiation which is received by means of infrared optics, for example a Cassegrain telescope or lens optics, coupled into the FTIR spectrometer, passed through a Michelson interferometer and focused onto the detector plane. By means of the interferometer, an interferogram is measured, which is converted into an infrared spectrum by Fourier transformation. The range of movement of the scanning mirror within the interferometer is typically in the range of 0.75 to 10 mm.

A suitable FTIR spectrometer uses, for example, cryo-cooled Mercury Cadmium Telluride (MCT) single detectors in combination with a radiometric calibration unit. Based on a radiometric calibration, the measured infrared spectrum is converted into a calibrated radiation temperature spectrum, which finds its way into the spectral evaluation algorithm.

For spectral evaluation, the spectral signatures of the target substance and of atmospheric interfering substances, such as water, $CO_2$ and other gases, as well as mathematical functions for modelling the background are calculated. As a result of this fitting calculation, the calculated signal height and the correlation coefficient of the calculated target substance signature are compared with substance-specific limit values. If predefined limit values are exceeded, the target substance is considered to be identified, which is done automatically and can lead directly to further actions by the system.

The principle of passive IR remote sensing works independently of artificial sources of radiation and functions both during the day and at night, regardless of location, direction of measurement and the time of year, by analysing the thermal radiation emitted by the environment in the direction of the spectrometer's bearing. The necessary condition for identifying a gas is the presence of at least a small temperature difference between the radiation temperature of the gas to be measured, i.e. the target substance, and the radiation temperature of the background in the direction of view or bearing. If the gas is warmer than the background in the direction of measurement, the spectral signature appears in emission, if it is colder than the background, in absorption.

Passive infrared remote sensing uses the long-wave spectral range of infrared radiation, for example in the wavenumber range of approx. 700-1,400 $cm^{-1}$. Within this atmospheric window, measurements are possible at long distances of up to several kilometres without the atmosphere causing too much attenuation of the signal. Limiting factors for the maximum measurement range are generally: the field of view of the detector due to existing obstacles, the size of the cloud to be measured and the attenuation of the signal along the optical measurement path due to the atmosphere, whereby a direct line of sight is always a prerequisite. In typical applications, measurements are taken with a measuring range of up to 1-5 km.

To detect an incident, it is first necessary to identify a target substance, i.e. an undesired gas. For this purpose, a corresponding output signal is generated at the output of the interferometer if the signal-to-noise ratio of the analysed measurement signal is sufficient. The identification of a target substance in a detected solid angle thus leads to the triggering of an incident case.

In addition, the quantification of the gas or target substance can be carried out in a passive single measurement in the form of the determination of a column density (unit ppm-m), i.e. the product of the density of the cloud and the cloud length in the direction of measurement. The column density thus corresponds to the density integrated along the measurement path.

For the spectral quantification of the column density, the approach via Lambert-Beer's law is possible under the assumption of a gas temperature and the consideration of the absorption cross-section of the target substance. An alternative approach is the quantification by means of a non-linear fitting algorithm, in which the gas temperature is also calculated as a model parameter.

Active measurement, in contrast to passive measurement, uses one or more remote active infrared radiation source(s) to increase the signal-to-noise ratio of the individual measurement. On the one hand, this enables the measurement of lower target substance concentrations and, on the other hand, the measurable spectral range of the measurement is extended, enabling a larger number of substances to be measured. The active measurement is limited in its viewing direction along the measurement path by the presence of a remotely placed radiation source and cannot be freely positioned at any time.

The active infrared radiation sources are preferably broadband emitters whose radiation is directed through infrared optics and which are aligned with the optical sensors. Narrow-band emitters can also be used.

For active measurement, the optical sensor is aligned with a directional infrared radiation source along the measurement path, typically installed at a distance of several tens to several hundreds of metres. The optical sensor receives the unmodulated, broadband infrared radiation from the source and measures an infrared spectrum. Gases that were located along the optical measurement path between the radiation source and the optical sensor at the time of measurement cause an absorption of the infrared radiation of the source depending on their substance-specific IR absorption cross-section, which depends significantly on the concentration of the target substance as well as the length of the cloud along the measurement path. The spectral thermal background is determined and subtracted from the measured spectrum.

By adding the active radiation source, the measurable spectral range is extended in the direction of short-wave, higher-energy light. The typical measuring range is in the wavenumber range of approx. 700-approx. 4,500 $cm^{-1}$.

The evaluation of the measured active infrared spectra is carried out by means of a spectral evaluation algorithm. Calibration of the system by means of defined gas concentration levels is not necessary for quantitative evaluation.

The bi- or multi-perspective system, which can also be called a monitoring system, is realised by combining at least two, preferably several passive FTIR spectrometers and optionally broadband emitting directional infrared radiation sources as well as a central server. This allows gas clouds to be identified and localised and gas concentrations to be quantified.

The system is used to locate hazardous areas in case of toxic or otherwise dangerous gases and for environmental monitoring of emission and immission levels within and/or along the perimeter of an area to be monitored.

The use of passive FTIR spectrometers for the remote detection of gases thus makes it possible to set up a monitoring system capable of monitoring distances. On the one hand, this makes it possible to achieve a high degree of coverage of the area. On the other hand, the adjustment of the monitoring area of the optical sensors is possible in real time and situation-related.

The remote gas detection system autonomously monitors areas of the area in a radius of, for example, up to 4 km per optical sensor. The number of combined optical sensors to the overall system is arbitrary, but at least two passively operating optical sensors are present.

For each optical sensor, the monitoring area is set up based on the topography of the area. On the one hand, the solid angle range to be monitored is defined in width and height and, on the other hand, the measuring radii are determined for all spatial directions. This is because the field of view of each optical sensor is limited by topographical obstacles such as area elevations, buildings and/or installations and their parts.

In addition, it is determined for each optical sensor which path within the monitoring area is to be scanned during the control case of the monitoring, i.e. which azimuth and elevation angles are to be traversed.

The use of the FTIR spectroscopic measurement method allows the detection and identification of a very large number of chemicals whose characteristic spectra are stored in a substance library on the server. In the case of the presence of a target substance of the substance library, the system identifies the location and, if necessary, also the temporal development of the dispersion and the direction of dispersion of the target substance gas cloud in space. For this purpose, at least two, if necessary also all optical sensors integrated in the system are automatically included in a situation-related situation assessment.

By measuring electromagnetic radiation over a very wide spectral range with high spectral selectivity, many different target substances can be clearly identified in the same measurement. The system's target substance database can include up to several hundred chemicals. Preferably, typical chemicals include ammonia, methanol, methane, chloroform and ethylene.

Thus, the system is suitable for many different scenarios and can be adapted to changing production processes, storage cycles of chemical warehouses or changing disturbing influences. In addition, the measured data of the infrared spectra represent a physical actual state, which is useful as substance detection and substance non-detection.

An evaluation algorithm on the server, in particular the evaluation and control unit, processes the substance information and spectral data of the optical sensors and the possibly determined column densities and controls the measurement process. The described control and coordination of the optical sensors minimises the monitoring time, incident-related potential gas detections are validated from all possible viewing directions, furthermore, potential incidents are distinguished from disturbance variables or individual detections and, in the presence of a potentially dangerous gas cloud, a specific and unambiguous alarm is issued.

In the event of an alarm or incident, gas clouds can be displayed in a 2D map and/or a 2D visualisation as an overlay of the gas cloud with a video image from the viewing direction of the optical sensor.

The extensive area is divided into predefined monitoring areas, which are scanned automatically by the respective individual systems along freely programmable measurement paths in routine cases, recurrently and independently of the other systems.

In case of an incident, i.e. after identification of a target substance by at least one optical sensor, selected neighbouring optical sensors are automatically consulted to verify the incident and to localise and quantify the gas cloud. In this way, a near-real-time map-based situation assessment of the incident is generated and made available, for example, to the emergency services.

The selection of the optical sensors to be used in case of an incident is based on a priori determined common monitoring areas or field of view areas, which result from the topography of the monitored area and the position of the optical sensors as well as from the viewing direction in which the incident was detected. The influence of the topography due to shadowing of the viewing areas of the optical sensors by area elevations, buildings and/or installations is taken into account so that no measurement values of the corresponding optical sensors can be obtained in the viewing direction behind a topographical obstacle. This topographical information has been taken into account when determining the respective monitoring area during the installation of the optical sensors.

The respective monitoring areas and the common overlapping monitoring areas of the installed optical sensors are thus calculated and stored at the time of installation, so that in the event of an incident they only need to be retrieved and compared with the line of sight of the incident; a recalculation of overlapping monitoring areas or field of view areas is not normally necessary.

On the basis of the known monitoring areas or field of view areas, the further optical sensors are automatically controlled to find the target. For this purpose, the at least one further optical sensor is controlled in such a way that it scans the monitoring area of the optical sensor triggering the incident.

The joint identification of a target substance from more than one measurement position thus enables the verification of a potential incident and the localisation of the identified target substance gas cloud in space by triangulation. Furthermore, the calculation of a spatial concentration distribution of the gas cloud can be performed. A downstream application of evaluation criteria for the automated interpretation of the measurement results based on a quality assessment of the measurement values as well as spatial and temporal parameters allows a reliable position assessment.

As a result, the measurement data is displayed on a map as a colour-coded position evaluation. In addition, the two-dimensional representation of the measurement results of selected optical sensors superimposed on the video image can be added at any time in the form of a temporal video stream.

As soon as an optical sensor or the system signals the identification of a target substance from the target substance library, the system leaves its routine operation and switches to target identification and subsequent situation assessment of a potential incident.

When a target substance is identified from the field of view of an optical sensor, at least one further optical sensor or the remaining optical sensors are coordinated to obtain further information. For this purpose, the predefined measurement paths are left until normal operation is resumed in routine mode.

The analysis of the local distribution function of the measurement signal provides angular ranges for which the presence of a gas cloud is more likely. These angular ranges are preferably sampled in higher local resolution.

Angular ranges can be classified into ranges in which (a) a target substance is identified, (b) angular ranges in which no identification is metrologically possible, and (c) angular ranges which allow a target substance to be identified metrologically and for which the target substance is not detected after evaluation of the identification algorithm with respect to the generated measurement signal and, if applicable, the minimum column density of the target substance. The classification of the monitoring ranges is substance-specific.

The representation of a monitoring area can be done in a map. Areas in a field of view of an optical sensor are shown in the map. In case of an identification of a target substance from the used target substance library, the field of view is marked in the map. In the case of localisation of a gas cloud by joint identification from more than one measurement position, the area in which the gas cloud is localised is marked in the map.

By analysing the distribution function of the measurement signals, the calculated column densities of the target substance, if applicable, as well as the analysis parameters for target substance identification and taking into account the detection limits for each measurement point, the respective solid angles can be determined in which each optical sensor identifying a target substance determines the highest column density of the target substance. This measured value is used to localise the potential point of the gas cloud with the highest target substance concentration.

In the case of joint substance identification of more than one optical sensor, a potential centre of gravity for the gas cloud can be determined from all solid angles for which a maximum column density has been determined. This metrologically determined point can further be classified based on the measurement parameters:

(a) Under the condition of a free field of view of the gas cloud from at least two measuring positions and under the condition that the determined column density for the potential centre of gravity of the gas cloud for each field of view of an optical sensor is greater than the detection limit of the other measuring points of the monitoring area, the detected point is the location of the gas cloud which has the highest concentration.

(b) If there are areas within the gas cloud which cannot be detected metrologically from at least two measurement positions either due to shadowing or due to a low detection limit for the respective solid angle under consideration, it is determined whether a common intersection point can be determined for the respective solid angles with the highest determined column density. Under the condition that the surrounding partial areas around the solid angle with the highest determined column density can be metrologically determined from at least two measurement positions, this intersection point is assumed to be the point of the highest concentration of the gas cloud after checking plausibility criteria for the gradient of the signal.

The system described above monitors large areas such as production areas of a chemical park or loading points such as ports in a fully automated manner when carrying out the described procedure. The system is designed to be operated by slightly trained personnel, e.g. in the control centre of a chemical plant. In addition, the system's situation assessment is prepared in such a way that clear, unambiguous information is recognisable at a glance. This information must be equally interpretable for the plant operator, the plant operator, the control centre of the plant fire brigade and all participants of a crisis team. The information must be readable quickly, unambiguously and without prior knowledge so that the system is useful as an early warning system in the event of an incident or disaster.

BRIEF DESCRIPTION OF THE DRAWINGS

In the following, the invention is explained by means of embodiment examples with reference to the drawing. The drawing shows FIG. 1 an example of a system according to the invention, FIG. 2a,b,c examples of optical sensors, FIG. 3 schematic representation of the solid angles of two optical sensors with maximum column densities of a target substance, FIG. 4 the illustration according to FIG. 3 additionally with all solid angles with increased column density of a target substance, FIG. 5 the illustration according to FIG. 4 with partial shading of a monitoring area, FIG. 6 cartographic representation of a harbour with a system with two optical sensors, FIG. 7 the illustration according to FIG. 6 with a localised incident, FIG. 8a cartographic representation of a chemical plant with a system of passive optical sensors and active measuring sections, FIG. 9a cartographic representation of another chemical plant with partial shading of the monitoring areas of three optical sensors, FIG. 10 the illustration from FIG. 9 with a changed location of the detected target substance cloud, FIG. 11 the illustration from FIG. 8 with a stationary sensor and with a mobile sensor for detecting a target substance cloud, and FIG. 12 an embodiment example with an optical sensor and with a mobile non-optical sensor.

DESCRIPTION OF THE INVENTION

In the following description of the various embodiments according to the invention, components and elements with the same function and the same mode of operation are given the same reference signs, even if the components and elements may differ in dimension or shape in the various embodiments.

Figure 1:
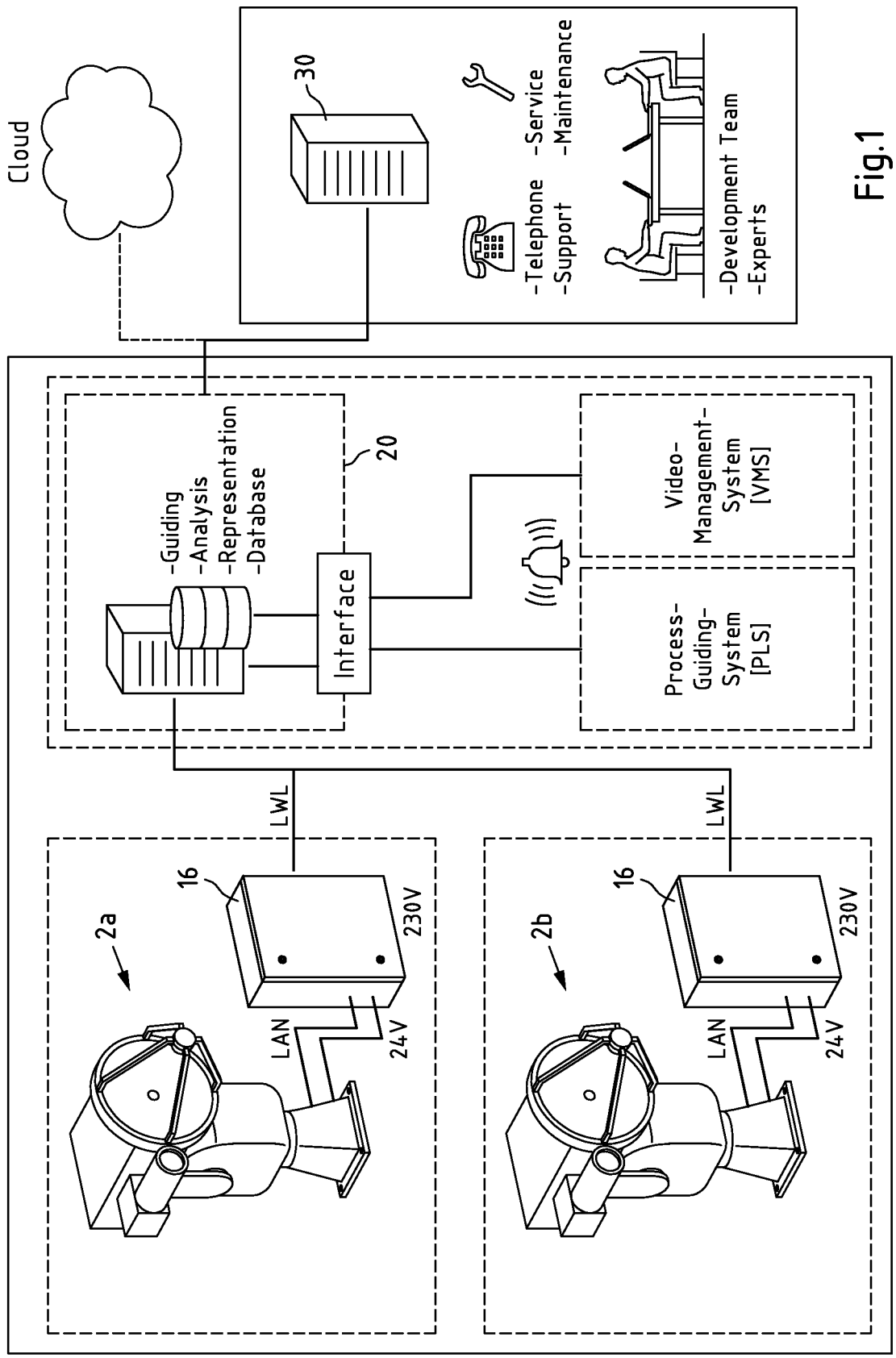

FIG. 1 shows a schematic structure of a system according to the invention for monitoring an airspace for an area.

Figure 2A:
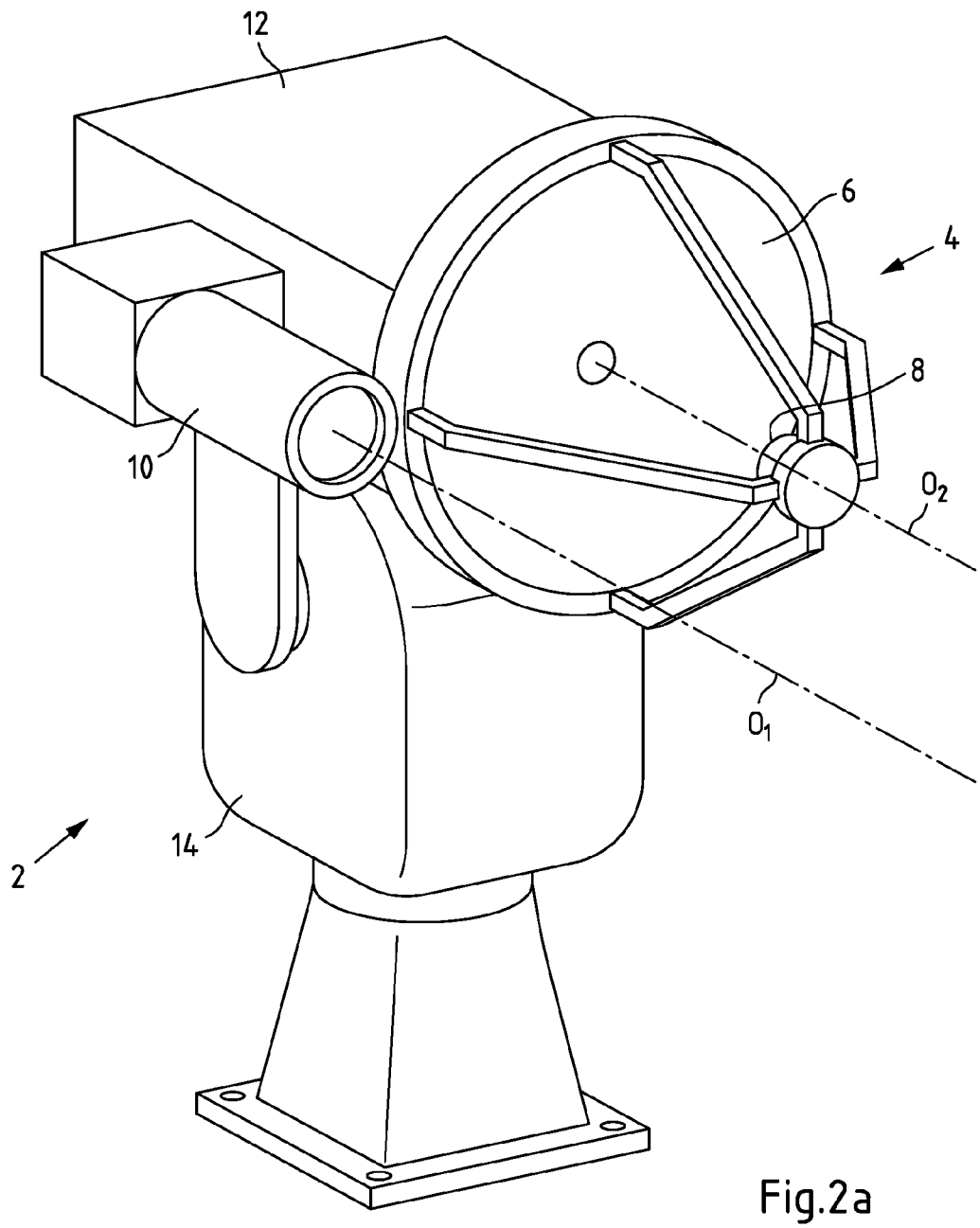
Figure 2B:
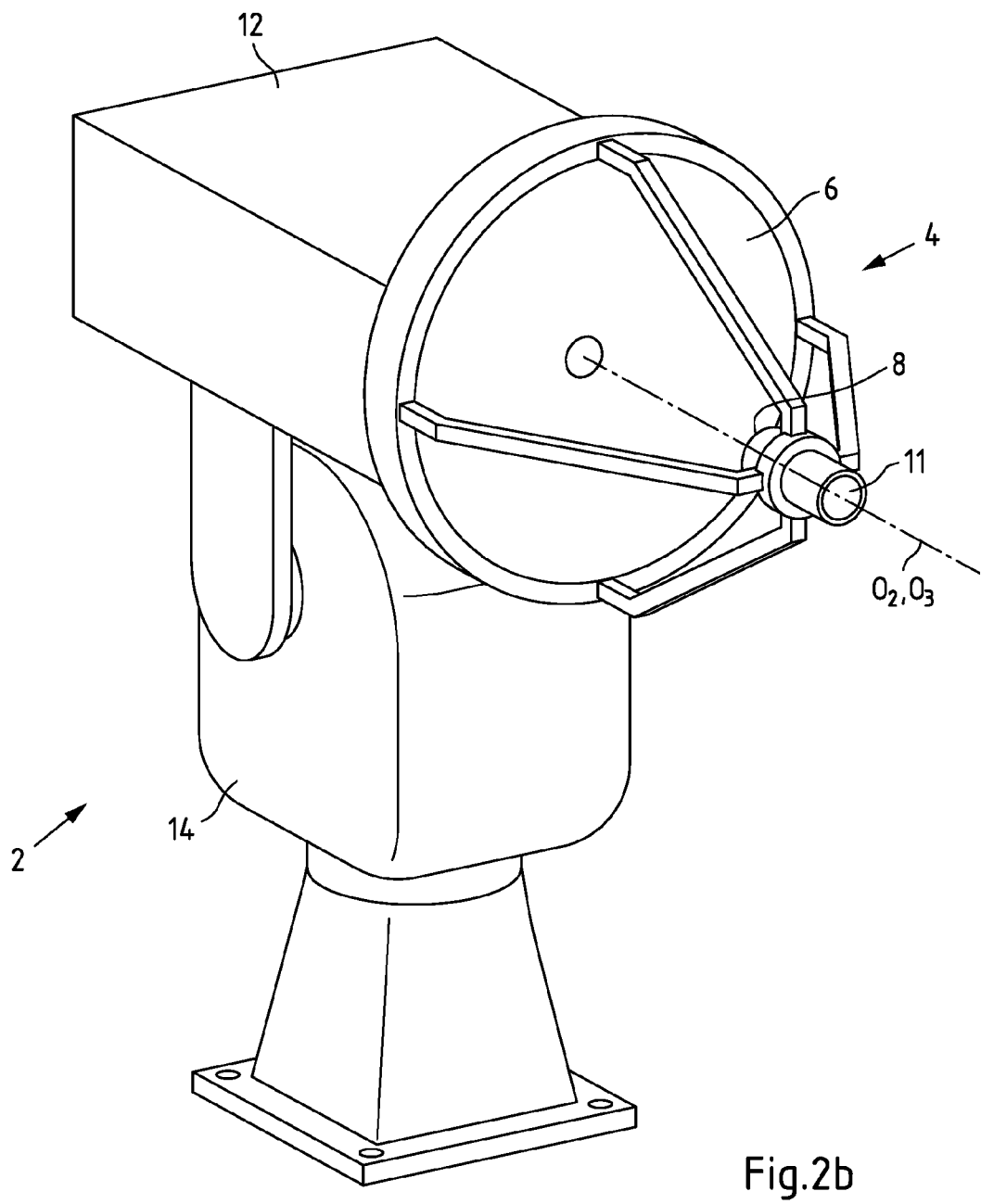
Figure 2C:
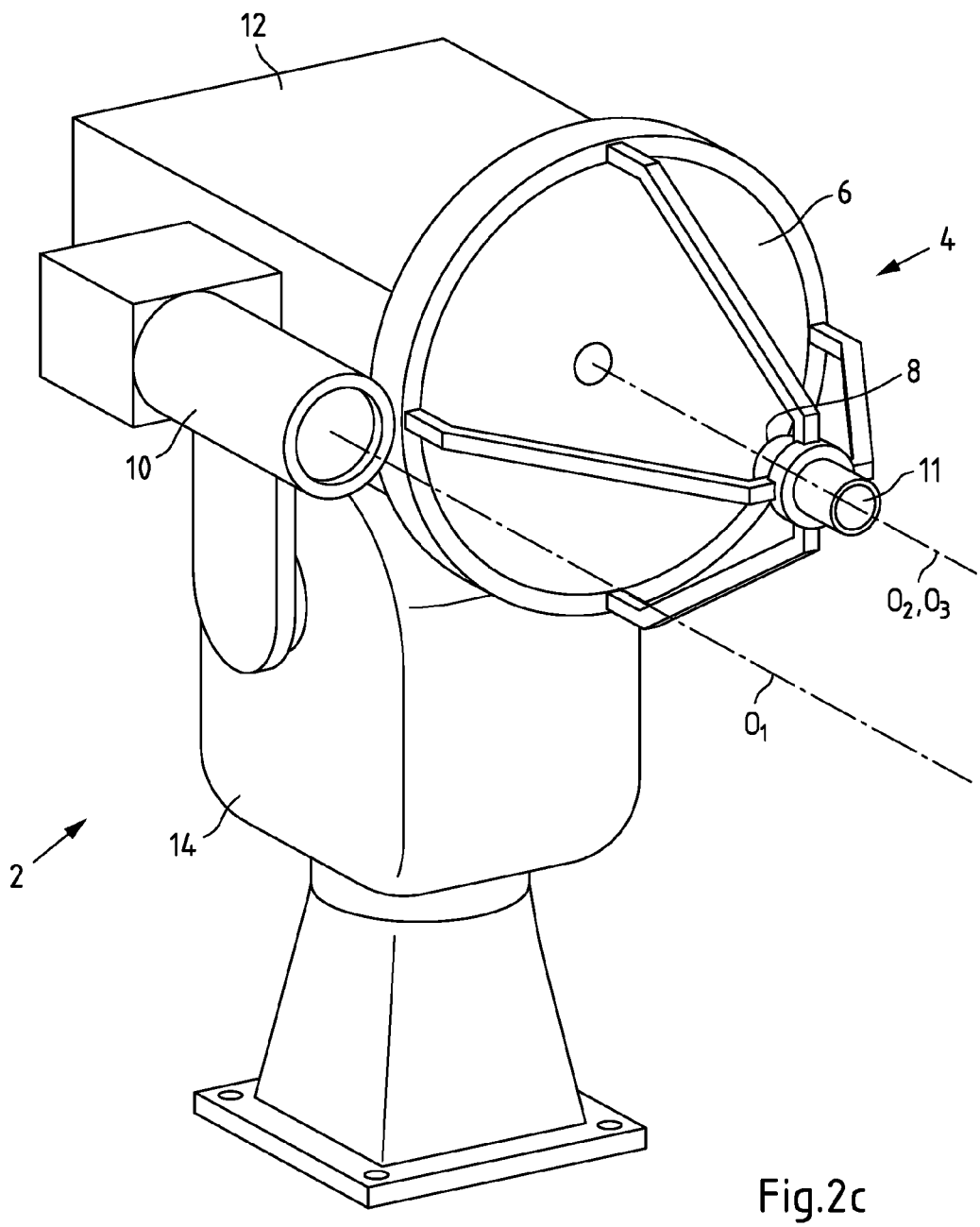

The system has two optical sensors 2a and 2b, which are shown in more detail in FIGS. 2a to 2c. Each optical sensor 2 (or 2a and 2b) basically has infrared optics 4 in the form of an IR telescope with parabolic mirror 6 and secondary mirror 8, a video camera 10 or 11, an FTIR spectrometer 12 and a controllable pan-tilt mimic 14 as a positioning unit.

The two optical sensors 2a and 2b are connected to a supply and interface device 16, which on the one hand provides the supply voltage of, for example, 24 volts for the optical sensors 2a and 2b. On the other hand, data transmission takes place by means of an Ethernet cable to a local area network (LAN). The device 16 can thus transmit control data to the optical sensors 2a or 2b on the one hand and receive the measurement data on the other hand. Alternatively, it can be provided that the interface device 16 and/or the sensors 2a, 2b receive the control data wirelessly and/or transmit the measurement data wirelessly.

Data is exchanged with a server 20 via fibre optic cables (LWL), in which computer programs for controlling the optical sensors 2a and 2b, for analysing and displaying the data and for storing the measurement data in particular in a database are stored and run.

Via an interface, the output information is forwarded to a process control system and a video management system located in the vicinity of the monitored area. Thus, an alarm can also be triggered here in the event of an incident (bell symbol) and at the same time the relevant information can be displayed to a user.

Furthermore, the system can also enable a transfer of data to a cloud application and/or have a direct data connection with an external server 30. The external server 30 can then be used for support functions (telephone, support, service, maintenance) and for supporting a development team with experts.

FIG. 2a shows the optical sensor 2 described above for monitoring an airspace for an area, with an FTIR spectrometer 12 for detecting target substances, with infrared optics 4 for imaging a partial section of the airspace of the area to be monitored onto the FTIR spectrometer 12, with a video camera 10 and with a positioning unit 14 for aligning the sensor unit formed by the FTIR spectrometer 12, the infrared optics 4 and the camera 10. In this case, the infrared optics 4 and the camera 10 detect essentially the same solid angle, in particular the optical axis $O_1$ of the infrared optics and the optical axis $O_2$ of the camera 10 are aligned parallel to each other.

In the embodiment shown, the infrared optics 4 is designed as a Cassegrain telescope with a parabolic mirror 6 and a secondary mirror 8. Alternatively, but not shown, the infrared optics can also be designed as lens optics.

The camera 10 is arranged laterally to the infrared optics 4 and therefore has sufficient installation space to be equipped with a telephoto lens to thus produce a high image quality of the monitored partial section of the airspace of the area. However, for an accurate overlay of the measurement data of target clouds, the parallax must be compensated by the distance of the optical axes.

FIG. 2b shows another example of an optical sensor 2. In contrast to FIG. 2a, a camera 11 is arranged in the optical axis of the infrared optics 4 at the front end of the secondary mirror. Thus the optical axis $O_2$ of the infrared optics 4 and the optical axis $O_3$ of the camera 11 coincide and a parallax effect is avoided. Due to the small size of the camera 11, which may be a smartphone camera, for example, the angle of observation is usually large, so that the angle of observation may be larger and the spatial resolution of the camera image smaller than with a camera with a telephoto lens. However, smartphone cameras with a telephoto function are already known, so that the camera 10 can be completely replaced.

FIG. 2c shows a further example of an optical sensor 2. In contrast to FIGS. 2a and 2b, the camera is designed as a camera system with a camera 10 arranged laterally to the infrared optics 4 and with a camera 11 arranged in the optical axis $O_2$ of the infrared optics 4. Thus, the optical axis $O_1$ of the camera 10 runs at a distance from the optical axis $O_2$ of the infrared optics 4, whereby the optical axis $O_3$ of the camera 11 coincides with the optical axis $O_2$ and thus has no or only a small distance therefrom.

Figure 3:
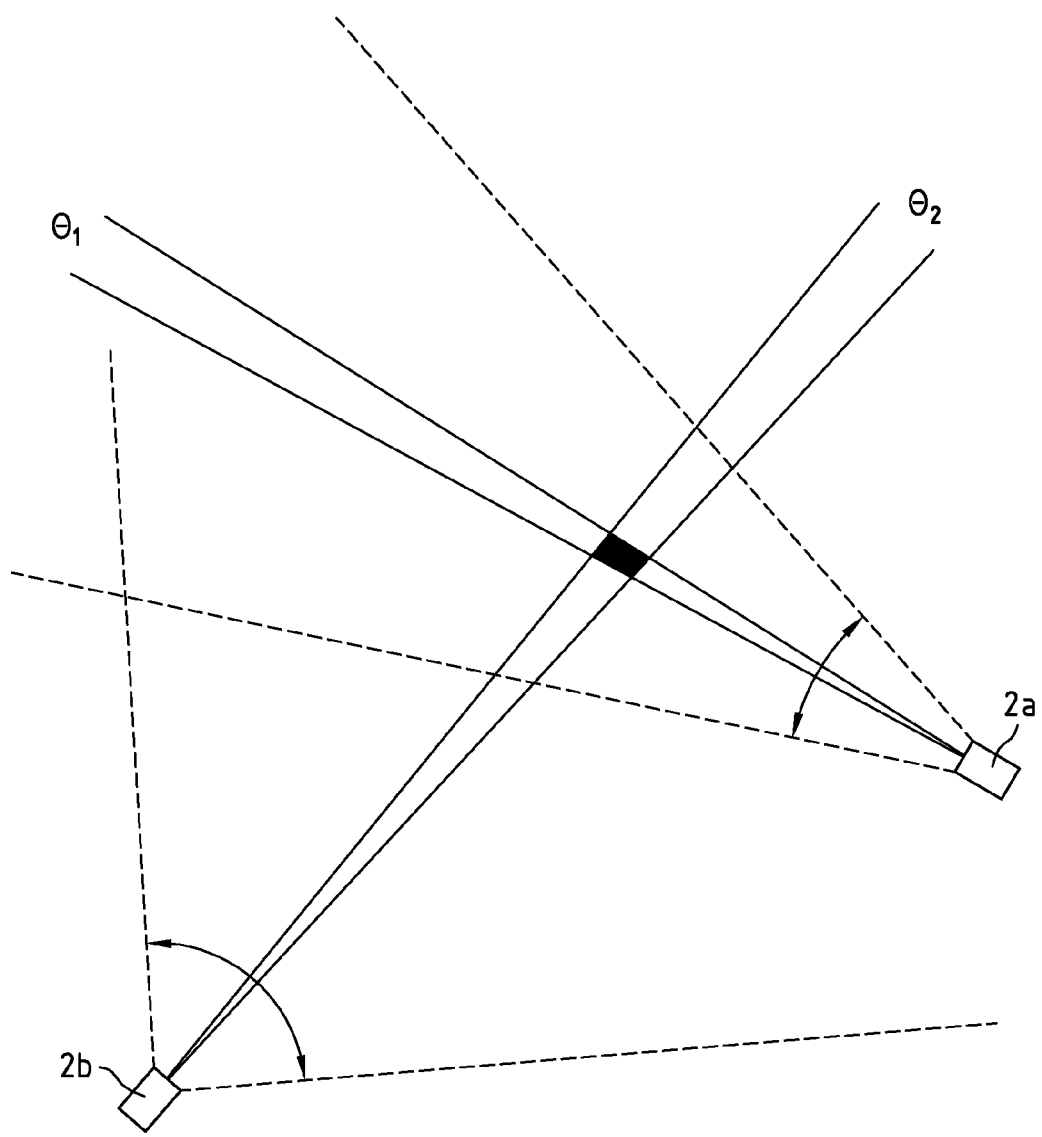

FIG. 3 shows a schematic representation of the monitoring by two optical sensors 2a and 2b. The first optical sensor 2a has a monitoring area which is marked with dashed lines and is approx. 35° wide. The optical sensor 2a usually scans the monitoring area at least partially along a predetermined path. The second optical sensor 2b has a monitoring range of approximately 90°, as also shown with dashed lines. The second optical sensor 2b also automatically scans the monitoring area at least partially along a preset path. Preferably, the scanning is repeated cyclically. The monitoring areas of both optical sensors overlap. During the measurements, the data is transferred to the server 30 and combined with the position data (solid angle).

The spectral intensity distribution of the received IR radiation is derived from the measurement data of the optical sensors 2a and 2b for each solid angle in order to identify at least one target substance by correlating the intensity distribution with known gas spectra. For this purpose, a corresponding computer program runs on the server 30 or, if applicable, in the optical sensor 2a or 2b.

In the event of an incident, i.e. when the first optical sensor 2a identifies a target substance, i.e. a gas of the target substance list in a solid angle $\Theta_1$, the further optical sensor 2b is triggered to scan the overlapping area with the monitoring area of the first optical sensor.

From the measurement data of the optical sensor 2b, a further solid angle $\Theta_2$ is identified with an infrared signal of the target substance, so that the coordinates of the overlapping area (black area) with increased concentration of the target substance can be determined from the solid angle information of the first solid angle $\Theta_1$ and the further solid angle $\Theta_2$.

Figure 4:
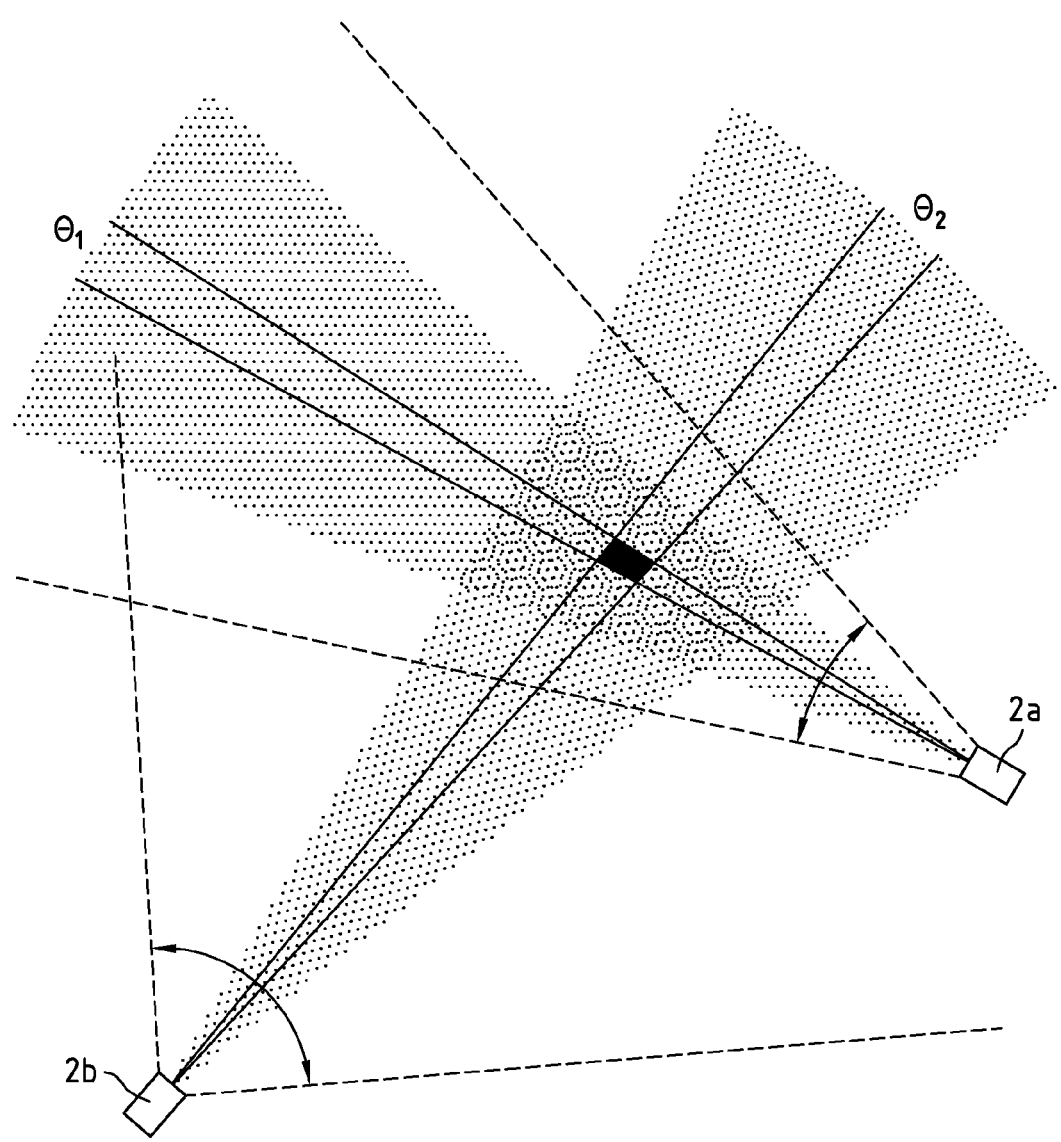

FIG. 4 shows an extended representation of FIG. 3, in which the dotted areas of the monitoring areas of the optical sensors 2a and 2b represent the solid angle areas in which at least a low concentration of the target substance has been identified. The solid angle areas $\Theta_1$ and $\Theta_2$ already shown in FIG. 3 show the solid angle areas with the highest concentration of the target substance, which has been determined by calculating the column density. For the calculation of the column density see the general description above. According to FIG. 4, not only the centre of the gas cloud of the target substance (black field), but also the expansion of the cloud can be determined.

Figure 5:
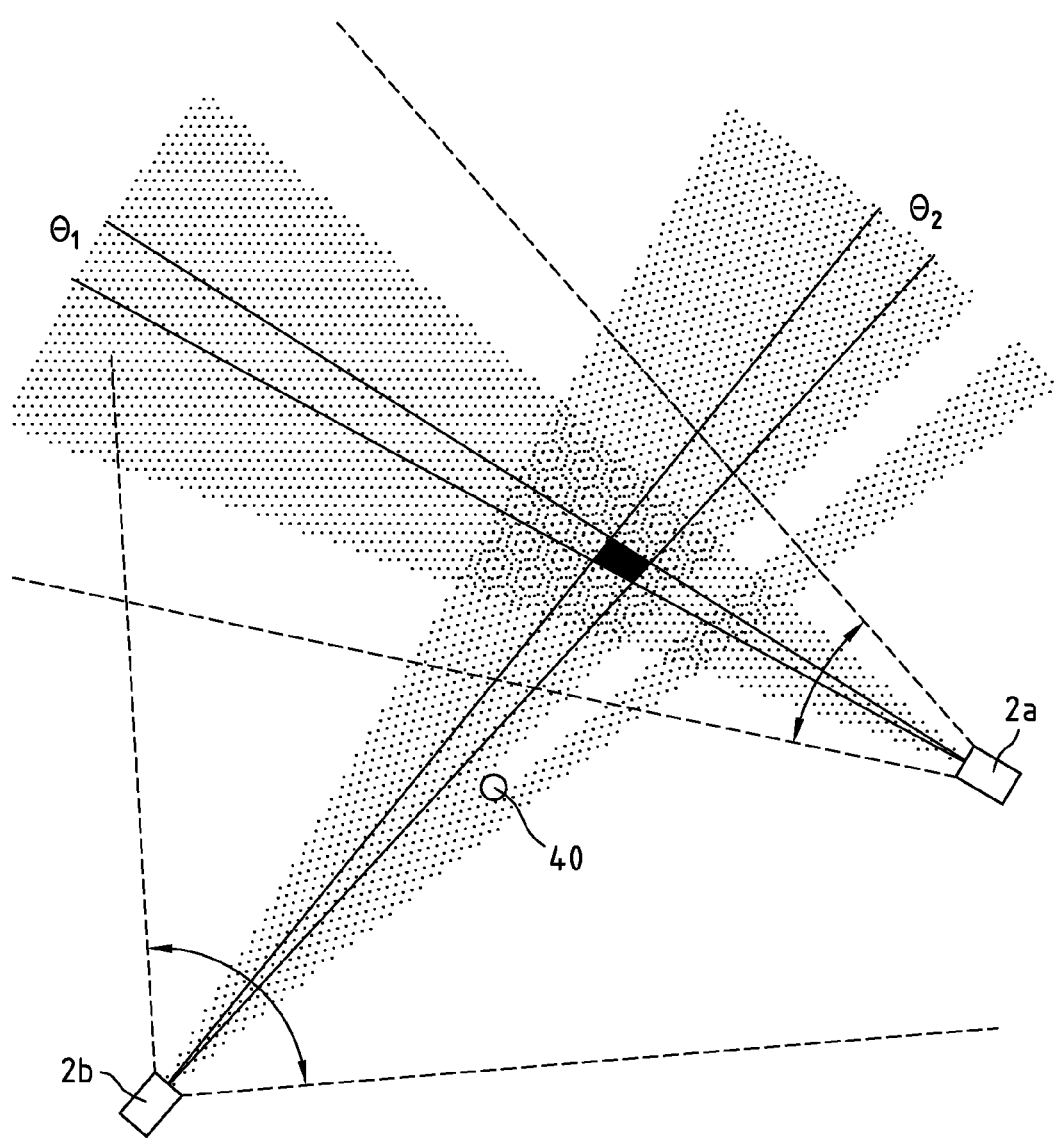

FIG. 5 shows a similar illustration as in FIG. 4. Here, a tower 40 is arranged on the monitored area in the monitoring area of the second optical sensor 2b, so that the area located by the optical sensor 2b behind the tower 40 is shadowed. The shadowed area can thus not be monitored by the optical sensor 2b, the measuring radius of the optical sensor 2b in this area only reaches up to the tower 40 and thus not up to the monitoring area of the optical sensor 2a. For this reason, the "shadow" is not dotted in FIG. 5.

When searching for the exact localisation of the cloud from the target material, the measurement signals of the optical sensor 2b in spatial directions with too small a measurement radius are not included in the evaluation. Here, the measurement radii are too small for the solid angles covered by the tower 40 and the monitoring areas of the sensors 2a, 2b do not overlap in a shadow behind the tower 40. Nevertheless, the extent of the cloud of the target substance can be almost completely detected. By not taking into account the measurement data in spatial directions with too small a measurement radius, the evaluation is not falsified, because in the monitoring area that ends at the tower 40, the measurement signal will not give any indication of the target substance, although this would be the case without the presence of the tower 40, see FIG. 4.

If necessary, the server 20 can be set up, i.e. by using computer programs, to replace the measurement signals of the further optical sensor 2b that have not been included in the evaluation by mathematical interpolation of adjacent measurement signals of the optical sensor 2b. Adjacent measurement signals are those whose assigned solid angle ranges are adjacent to the solid angle ranges of the measurement signals that have not been included.

Figure 6:
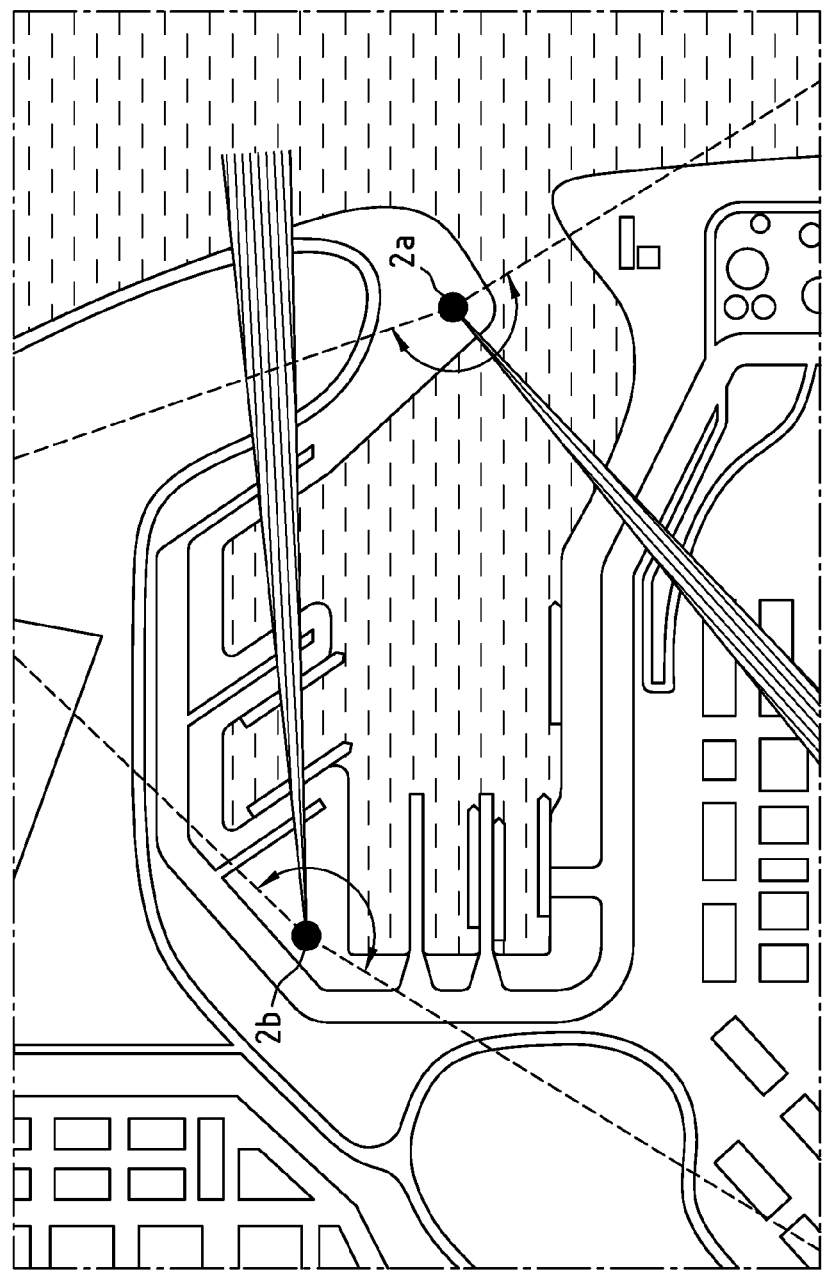
Figure 7:
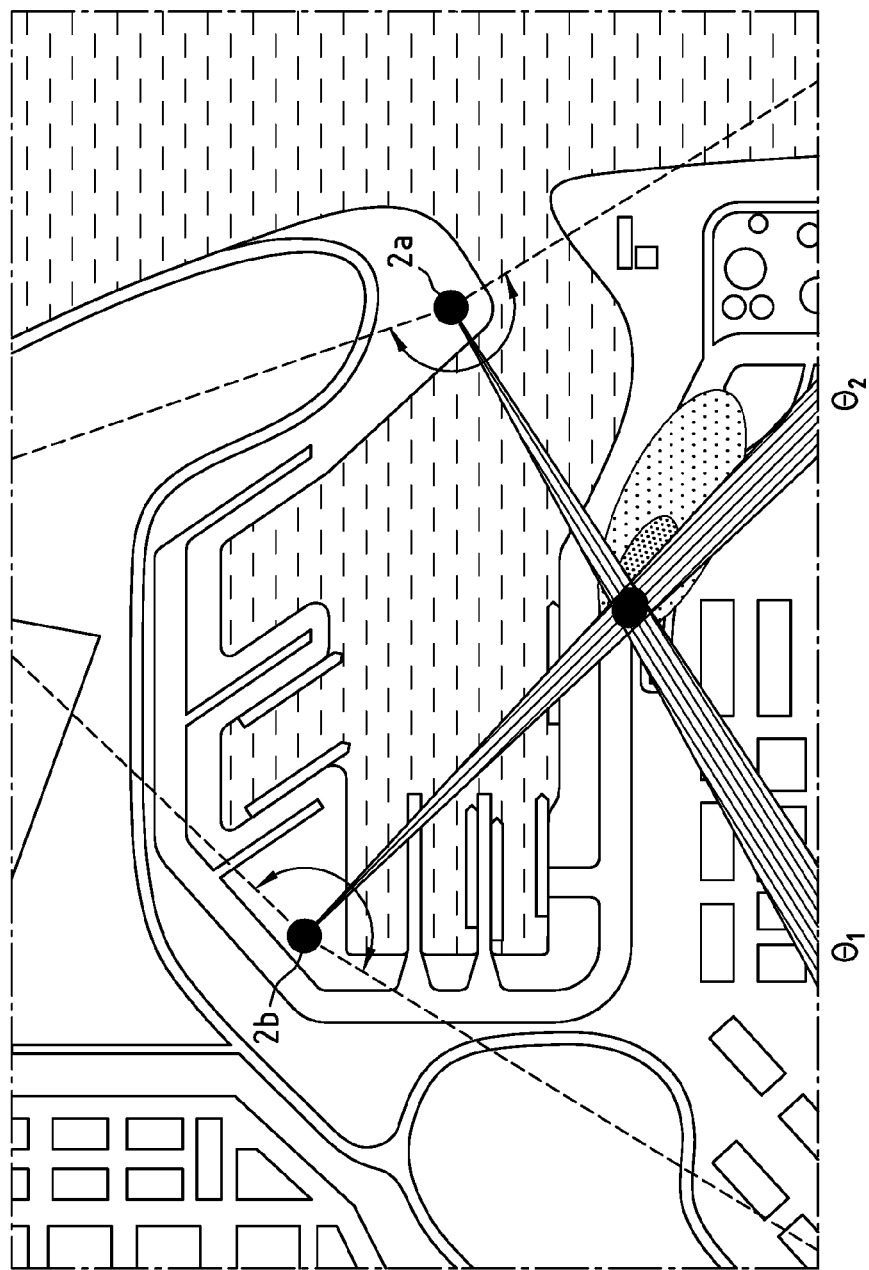

FIGS. 6 and 7 show a system for monitoring an airspace of a harbour basin area in which the two optical sensors 2a and 2b are positioned at prominent positions within the harbour area.

FIG. 6 shows the standard case in which the two optical sensors 2a and 2b independently scan the airspace above the area within the monitoring areas marked with dashed lines.

FIG. 7 shows the incident case as described above. The server 20 is set up by using a computer program to determine the coordinates of the overlap area (black area in FIG. 7) of the solid angle areas $\Theta_1$ and $\Theta_2$ of the highest column densities of the two optical sensors 2a and 2b and to link the coordinates with a map representation and to create a two-dimensional representation of the incident. Preferably, a three-dimensional representation can also be created by linking with images from the cameras 11 of the sensors 2a, 2b.

Figure 8:
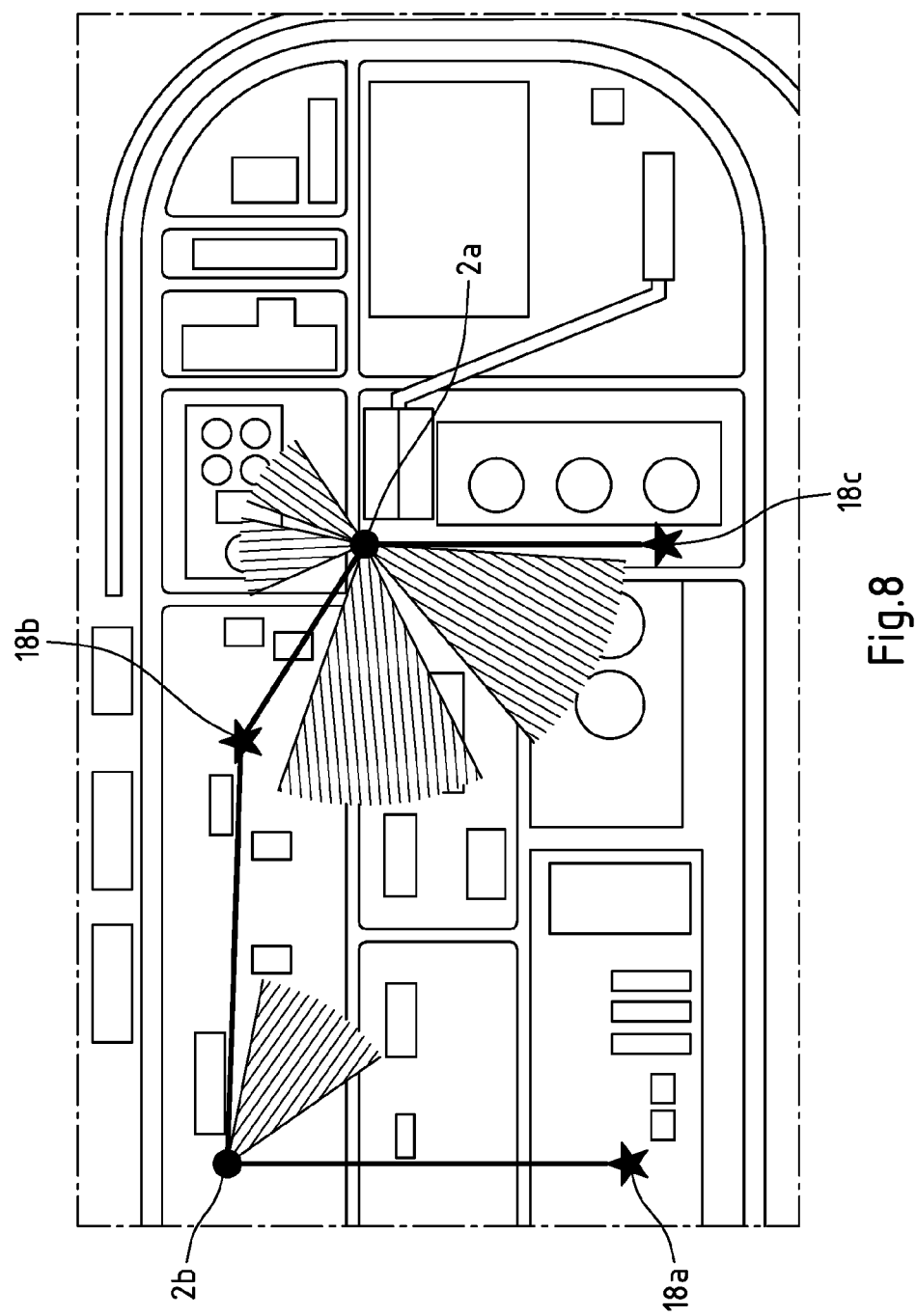

FIG. 8 shows another system for monitoring an airspace for an extensive chemical production area. Again, two optical sensors 2a and 2b are arranged at prominent positions. In addition, three active infrared radiation sources 18a, 18b and 18c are arranged in such a way that one of each of the optical sensors 2a or 2b picks up the infrared light. This enables a more precise measurement of the gases contained in the atmosphere along the established measurement paths (thick lines in FIG. 8). Furthermore, the spectral range for evaluation can also be broadened, which allows a larger number of target substances to be measured. Among other things, the active measurements enable a more precise background determination of the gas distribution as well as a larger target substance library. Furthermore, the active infrared radiation sources 18a, 18b, 18c enable separate monitoring of predefined boundary areas, such as plant boundaries.

Figure 9:
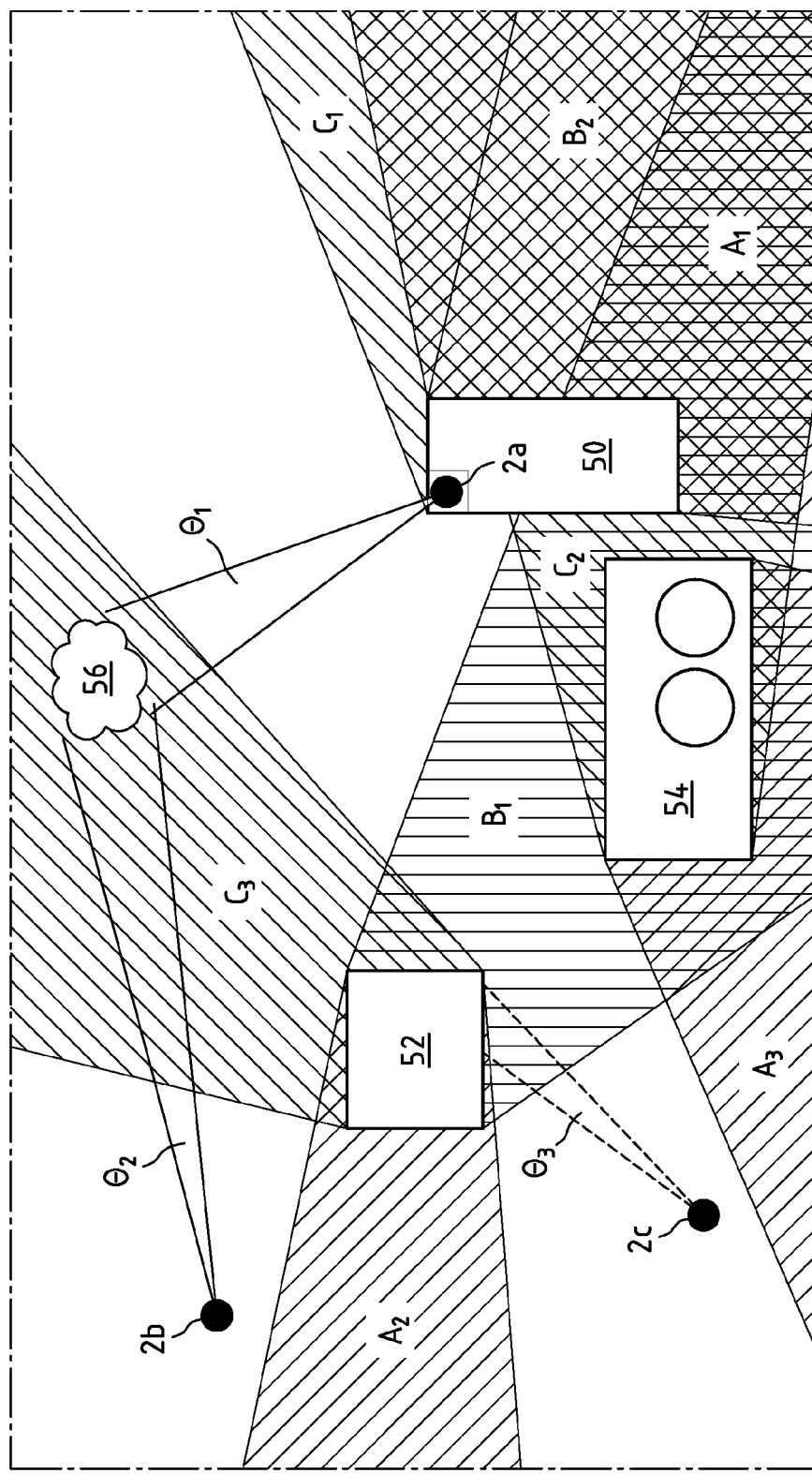

FIG. 9 shows a cartographic representation of another chemical plant with partial shading of the monitoring areas of three optical sensors 2a, 2b and 2c.

There are buildings 50, 52 and 54 on the premises which partially shade the monitoring area of the optical sensor 2a, resulting in shadow areas $A_1$, $A_2$ and $A_3$ respectively. The monitoring range of the optical sensor 2a therefore only extends as far as the building 50, 52 or 54 in each of the assigned spatial angles.

In the same way, shading areas $B_1$ and $B_2$ result for optical sensor 2b and shading areas $C_1$, $C_2$ and $C_3$ for optical sensor 2c.

FIG. 9 shows the system with the three optical sensors 2a, 2b and 2c with a target substance cloud 56. The target substance cloud 56 is detected first by the sensor 2a in the normal case of the scanning optical sensors 2a, 2b and 2c and an incident case is determined.

The server not shown in this figure is set up to select at least one further optical sensor $2b$ for activation in this incident, whose monitoring range has a maximum overlap with the monitoring range of the first optical sensor $2a$. The shadows $B_1$ and $B_2$ lie outside the solid angle range $\Theta_1$ of the first optical sensor $2a$, so that a maximum overlap is given by the monitoring range of the sensor $2b$. The second sensor $2b$ then detects the target substance cloud 56 within the solid angle range $\Theta_2$ and the target substance cloud 56 is localised.

The third sensor $2c$ is not selected in this scenario because the shadowing area $C_3$ overlaps part of the solid angle range $\Theta_1$. A selection of the optical sensor $2c$ would then also not have led to a positive measurement of the target substance cloud 56, because the target substance cloud 56 lies completely in the shadowing area C. The measurement radius of the third sensor $2c$ is therefore too small here in the solid angle range $\Theta_3$. The potential solid angle $\theta_3$ is only shown as a dashed line because the shadowing by the building 52 prevents measurement of the target substance cloud 56.

Figure 10:
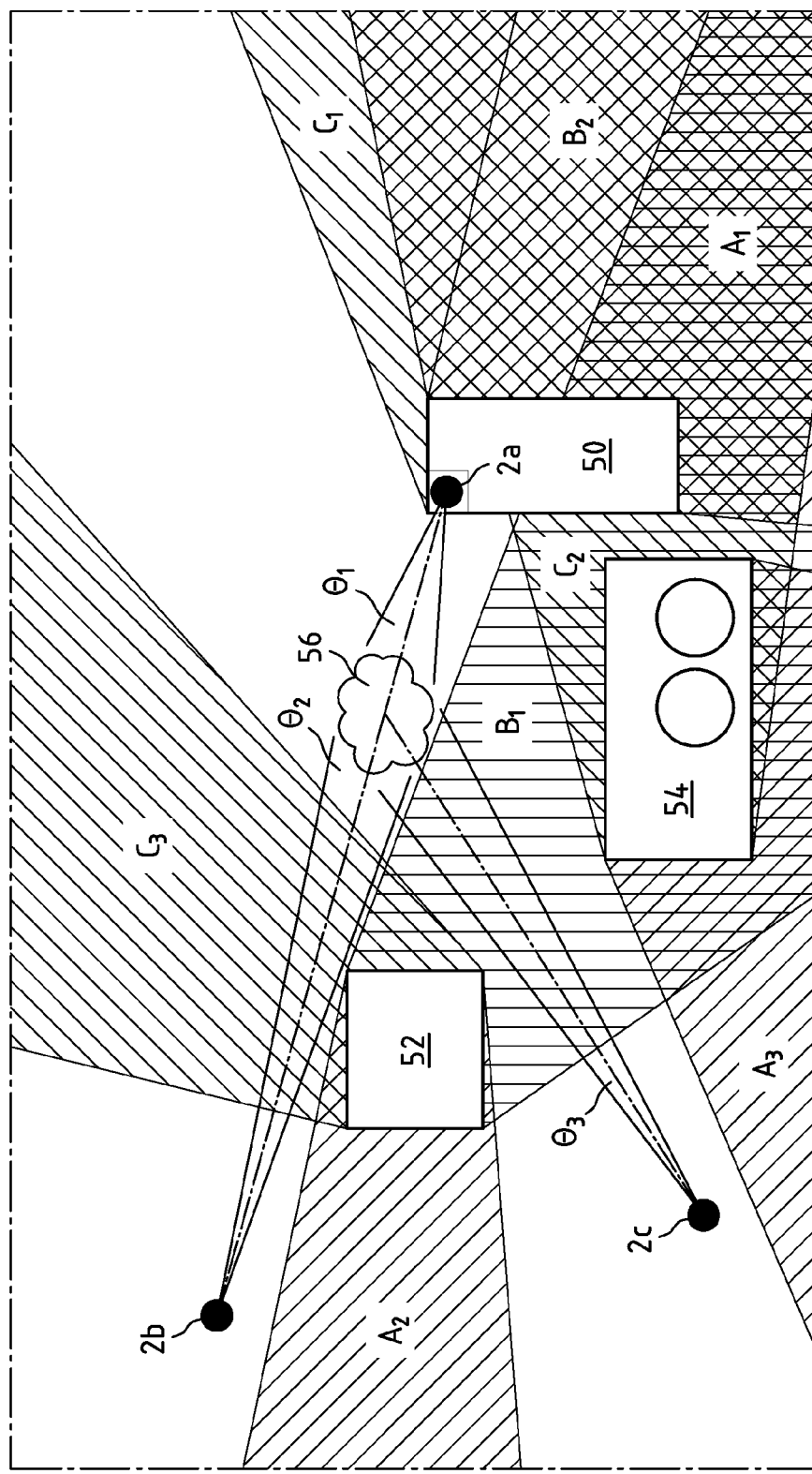

FIG. 10 shows the illustration from FIG. 9 with a changed location of the detected target substance cloud 56.

After the optical sensor $2a$ has detected the target substance cloud, the server searches for another optical sensor to achieve the localisation of the target substance cloud 56. It is found that both optical sensors $2b$ and $2c$ each have a shadowing area that overlaps with the solid angle area $\Theta_1$. However, the optical sensor $2b$ is not selected by the server because the position of the optical sensor $2b$ is in the direction of the solid angle range $\Theta_1$ of the first optical sensor $2a$ with detected target substance. Therefore, the third optical sensor $2c$, whose monitoring area has solid angles with a larger angle to the measured solid angle area $\Theta_1$ of the first optical sensor $2a$, is selected to identify the target substance cloud 56, determine the solid angle area $\Theta_3$ and thus the coordinates of the target substance cloud 56.

Figure 11:
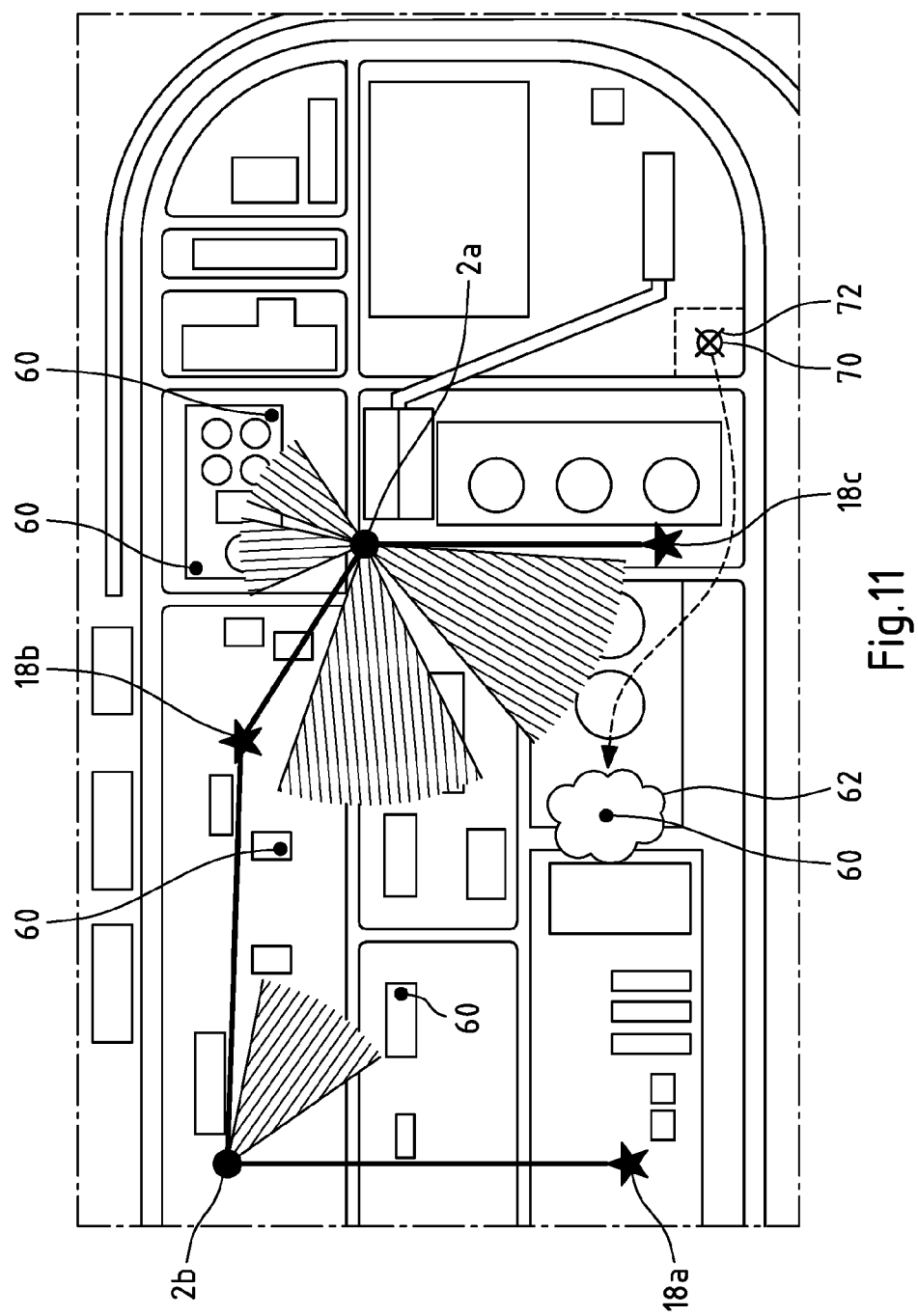

FIG. 11 shows a further example of an embodiment of a system according to the invention, which is based on the embodiment according to FIG. 8.

In addition to the embodiment of the system described above, it is additionally provided here that stationary detectors 60, which are designed as chemo-electric detectors. The server (not shown here) is set up to use an output signal of the at least one stationary detector 60 as a triggering signal for the use of the optical sensors $2a$, $2b$ in the spatial area of the stationary detector. A plurality of detectors 60 are shown, all of which are positioned in solid angle ranges that can be detected by the optical sensors $2a$ and $2b$. Even though several detectors 60 are shown here, it is sufficient within the scope of the invention if only one detector 60 is present.

If an incident occurs with a leakage of a target substance and a cloud 62 spreads, then the detector 60 located in the cloud 62 can detect the target substance and send a corresponding signal to the server. Subsequently, the two optical sensors $2a$ and $2b$, if they have not yet detected the incident, can detect the gas cloud 62 and process it as described above.

As can be seen in FIG. 11, at least one mobile sensor 70 can be mounted on a drone 72. The mobile sensor 70 can be an optical sensor 2 or a detector 60. As shown with a dashed line, the mobile sensor 70 is guided to the cloud 62 in the event of an incident and can make additional measurements on site, which can be evaluated by the system and the server.

If the mobile sensor 70 has an optical sensor 2, then the measurement signal from the mobile sensor 70 can be evaluated together with the measurement signals from the other stationary optical sensors $2a$ and $2b$, as described previously.

If the mobile sensor 70 has a detector 60, then the variability of the positions of the mobile sensor 70 allows further data to be collected in addition to the readings from the stationary detector 60.

Figure 12:
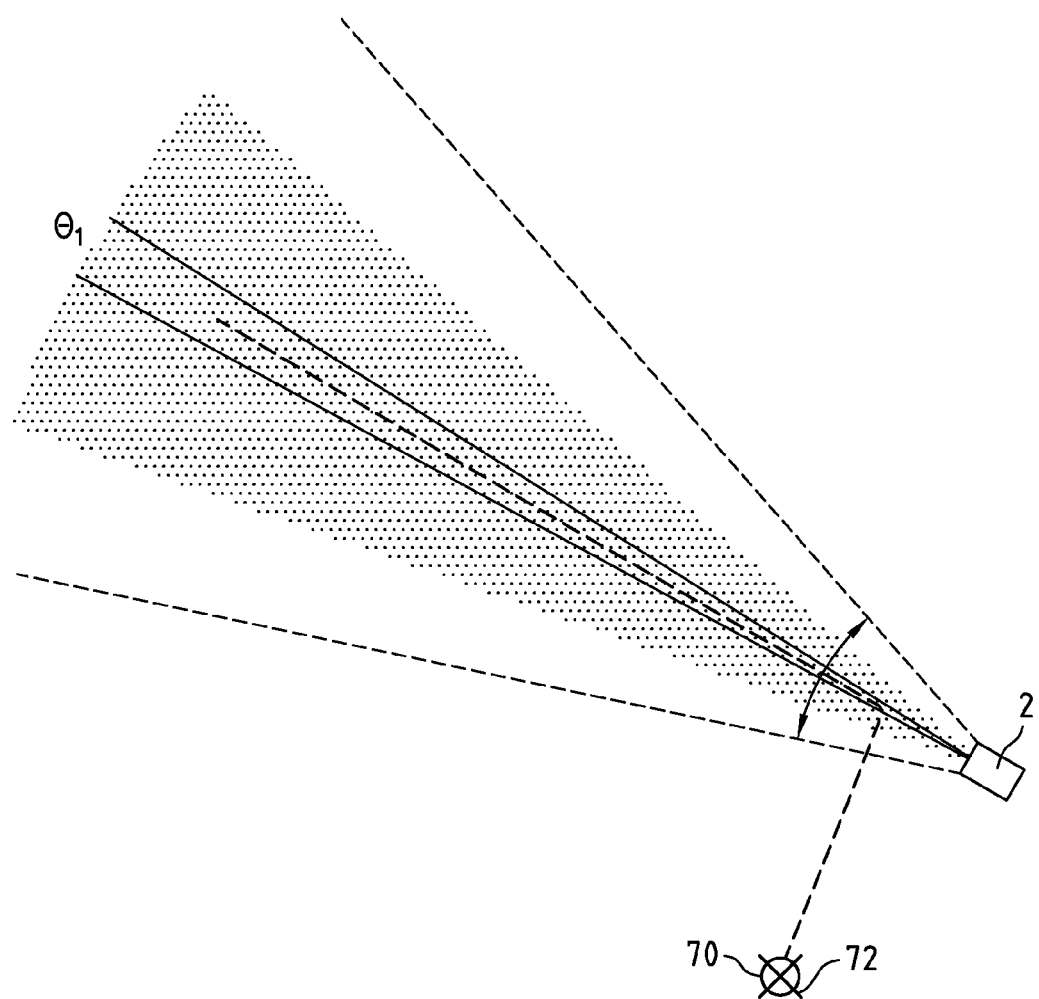

FIG. 12 shows a further example of a system according to the invention. This system corresponds essentially to the system in FIG. 4, but only one optical sensor 2 with a passive Fourier transform infrared spectrometer is present. As described above, a server (not shown) is provided for evaluating the measurement data and for controlling the optical sensor 2. The optical sensor 2 has—as described—an adjustable monitoring range.

A mobile airworthy sensor 70 of the type described above is provided, which is attached to a drone 72 described above. In case of an incident, i.e. when the optical sensor 2 identifies a target substance in a solid angle (shown dotted) whose column density is highest within the angle $\Theta_1$, the mobile sensor 70 is controlled by the server to detect the concentration of the target substance along the solid angle identified by the optical sensor 2 in a location-dependent manner. The corresponding flight path is shown in dashed lines in FIG. 12.

Thus, with only one optical sensor 2 and one mobile sensor 70, the location of the maximum concentration of the target substance, shown as a black area, can be determined.

What is claimed is:

1. A system for monitoring an airspace of an area,
   with at least two optical sensors with a passive Fourier transform infrared spectrometer and
   with a server for evaluating the measurement data and for controlling the at least two optical sensors,
   wherein each optical sensor has an adjustable monitoring range and wherein the monitoring ranges of the at least two optical sensors overlapping at least in sections, and
   wherein the server is set up,
   to control the optical sensors in the normal case for an automatic scanning of the monitored areas, wherein the server assigns to the measurement data in each case a solid angle on the basis of the position data of the optical sensor,
   deriving the spectral intensity distribution of the received IR radiation from the measurement data of the optical sensors for each solid angle and identifying at least one target substance by means of correlation of the intensity distribution with known gas spectra,
   in case of an incident, when a first optical sensor identifies a target substance in a first solid angle, to control at least one further optical sensor to scan the overlapping area with the monitoring area of the first optical sensor,
   identifying from the measurement data of the at least one further optical sensor at least one further solid angle with an infrared signal of the target substance, and
   determining the coordinates of the overlap area with increased concentration of the target substance from the solid angle information of the first solid angle and the at least one further solid angle,
   wherein the monitoring range of each optical sensor has different measuring radii due to the topography and/or the development of the area as a result of shadowing depending on the solid angle, and the monitoring range of each optical sensor is defined by the solid angle range and the associated measuring radii,
   that the measuring radii per solid angle are determined and set during the installation of the system for the optical sensors based on the known topography and/or development of the area and wherein the measurement signals of the at least one further optical sensor in spatial directions with too small a measurement radius are not included in the evaluation.

2. The system according to claim 1,
wherein the server is set up to replace the measurement signals of the at least one further optical sensor which have not been included in the evaluation by a weighted mathematical interpolation of spatially adjacent measurement signals.

3. The system according to claim 1,
wherein at least three optical sensors are provided and that the server is set up to select, in the event of an incident, at least one further optical sensor for activation whose monitoring range has a maximum overlap with the monitoring range of the first optical sensor.

4. The system according to claim 1,
wherein the server is set up to determine the column densities of the target substance from the measurement data of the optical sensors, the column density being the mathematical product of the concentration of the gas and the spatial length of the gas cloud, and
that the server is set up to determine the coordinates of the overlapping area of the highest column densities of different optical sensors.

5. The system according to claim 1,
wherein at least one stationary detector is provided and the server is set up to use an output signal of the at least one stationary detector as a triggering signal for the deployment of the optical sensors in the spatial area of the stationary detector.

6. The system according to claim 1,
wherein at least one sensor is designed as a mobile sensor, the mobile sensor being designed as an optical sensor or as a detector.

7. A system for monitoring an airspace of an area,
with at least one optical sensor with a passive Fourier transform infrared spectrometer and
with a server for evaluating the measurement data and for controlling the at least one optical sensor,
wherein the at least one optical sensor has an adjustable monitoring range,
wherein at least one mobile airworthy detector is provided and
the server is set up,
to control the optical sensor to automatically scan the monitoring areas, wherein the server assigns a spatial angle to the measurement data in each case on the basis of the position data of the optical sensor,
to derive the spectral intensity distribution of the received IR radiation for each solid angle from the measurement data of the optical sensor and identifying at least one target substance by means of correlation of the intensity distribution with known gas spectra,
in which the measuring radii per solid angle are determined and set during the installation of the system for the optical sensors based on the known topography and/or development of the area and
in case of an incident, when the optical sensor identifies a target substance in a solid angle, to detect the concentration of the target substance along the solid angle identified by the optical sensor with the at least one mobile detector in a location-dependent manner.

8. The system according to claim 7,
wherein the server locates the target substance in the event of an incident by determining that position of the mobile sensor in the monitoring range of the first sensor for which the concentration of the target substance is maximum.

9. A method for monitoring an airspace of an area,
in which at least two optical sensors with a passive Fourier transform infrared spectrometer are used to monitor the area at least in sections,
in which each optical sensor detects adjustable solid angle ranges within a monitoring are,
in which the monitoring area of an optical sensor overlaps at least in sections with the monitoring area of at least one further optical sensor,
in which the optical sensors are usually triggered to automatically scan the monitored areas,
in which the spectral intensity distribution of the received IR radiation is derived from the measurement data of the optical sensors for each solid angle and a correlation of the intensity distribution with known gas spectra is carried out,
in which, in the event of an incident, when an infrared signal of a target substance is identified by a first optical sensor in a first solid angle, at least one further optical sensor is triggered to scan the overlapping area with the monitoring area of the first optical sensor,
in which at least one further solid angle with an infrared signal of the target substance is identified from the measurement data of the at least one further optical sensor, and
in which the coordinates of the overlap area with increased concentration of the target substance are determined from the solid angle information of the first solid angle and of the at least one further solid angle,
that the monitoring range of each optical sensor has different measuring radii due to the topography and/or the area of the terrain as a result of shadowing depending on the solid angle and the monitoring range of each optical sensor is determined and fixed by the solid angle range and the associated measuring radii,
in which the measuring radii per solid angle are determined and fixed during the installation of the system for the optical sensors on the basis of the known topography and/or development of the area and
wherein measurement signals of the at least one further optical sensor in spatial directions with too small a measurement radius are not included in the evaluation.

10. The method according to claim 9,
in which the measurement signals of the at least one further optical sensor which have not been included in the evaluation are replaced by mathematical interpolation of adjacent measurement signals.

11. The method according to claim 9,
in which at least three optical sensors are used,
in which an infrared signal of a target substance is identified by the first sensor in the first solid angle, and
in which, in the event of an incident, at least the further optical sensor whose monitoring range has a maximum overlap with the monitoring range of the first optical sensor is selected for activation.

12. The method according to claim 9,
in which the column density is calculated as the mathematical product of the concentration of the gas and the spatial length of the gas cloud and
in which the coordinates of the overlap area of the highest column densities of different optical sensors are determined.

* * * * *

UNITED STATES PATENT AND TRADEMARK OFFICE
CERTIFICATE OF CORRECTION

PATENT NO. : 11,674,895 B2  
APPLICATION NO. : 17/641255  
DATED : June 13, 2023  
INVENTOR(S) : René Braun et al.

Page 1 of 1

It is certified that error appears in the above-identified patent and that said Letters Patent is hereby corrected as shown below:

In the Claims

Column 24, Line 9, Claim 9, delete "are," and insert -- area, --

Signed and Sealed this
Eighth Day of August, 2023

Katherine Kelly Vidal  
*Director of the United States Patent and Trademark Office*